(12) United States Patent
Takagi

(10) Patent No.: US 9,795,363 B2
(45) Date of Patent: Oct. 24, 2017

(54) ULTRASOUND DIAGNOSTIC APPARATUS AND METHOD FOR OUTPUTTING ULTRASOUND DIAGNOSTIC IMAGE

(71) Applicant: KONICA MINOLTA, INC., Tokyo (JP)

(72) Inventor: Kazuya Takagi, Osaka (JP)

(73) Assignee: KONICA MINOLTA, INC., Tokyo (JP)

( * ) Notice: Subject to any disclaimer, the term of this patent is extended or adjusted under 35 U.S.C. 154(b) by 263 days.

(21) Appl. No.: 13/691,955

(22) Filed: Dec. 3, 2012

(65) Prior Publication Data
US 2013/0090557 A1    Apr. 11, 2013

Related U.S. Application Data

(63) Continuation of application No. PCT/JP2012/001967, filed on Mar. 22, 2012.

(30) Foreign Application Priority Data

Apr. 5, 2011    (JP) .................................. 2011-083302

(51) Int. Cl.
*A61B 8/08*    (2006.01)
*G01S 7/52*    (2006.01)
(Continued)

(52) U.S. Cl.
CPC ................ *A61B 8/481* (2013.01); *A61B 8/08* (2013.01); *A61B 8/085* (2013.01); *A61B 8/14* (2013.01);
(Continued)

(58) Field of Classification Search
CPC .......... A61B 8/481; A61B 8/08; A61B 8/085; A61B 8/14; A61B 8/463; A61B 8/5207;
(Continued)

(56) References Cited

U.S. PATENT DOCUMENTS

| 5,577,505 A | 11/1996 | Brock-Fisher et al. |
| 5,632,277 A | 5/1997 | Chapman et al. |

(Continued)

FOREIGN PATENT DOCUMENTS

| JP | 05-168626 | 7/1993 |
| JP | 2004-321688 | 11/2004 |

(Continued)

OTHER PUBLICATIONS

International Search Report issued May 15, 2012 in International (PCT) Application No. PCT/JP2012/001967.

(Continued)

*Primary Examiner* — Katherine Fernandez
*Assistant Examiner* — Katherine McDonald
(74) *Attorney, Agent, or Firm* — Holtz, Holtz & Volek PC

(57) ABSTRACT

An ultrasound diagnostic apparatus which includes: an imaging unit which forms images of a subject; a motion detection region setting unit which selects a first image from among the images which include images of the ultrasound contrast agent, selects a second image from among the images which do not include images of the ultrasound contrast agent, and sets, as a motion detection region, a region in which an amount of image change between the first image and the second image is smaller than a predetermined amount; and an output unit which outputs, as the ultrasound diagnostic image, the second image on which a position adjustment has been performed to match a position of the motion detection region set by the motion detection region setting unit and a position of a region included in the second image and similar in an image feature to the motion detection region.

22 Claims, 16 Drawing Sheets

(51) Int. Cl.
   *G01S 15/89* (2006.01)
   *A61B 8/14* (2006.01)
   *A61B 8/00* (2006.01)

(52) U.S. Cl.
   CPC ............ *A61B 8/463* (2013.01); *A61B 8/5207* (2013.01); *A61B 8/5246* (2013.01); *G01S 7/52039* (2013.01); *G01S 7/52057* (2013.01); *G01S 15/8963* (2013.01); *A61B 8/461* (2013.01); *G01S 15/8979* (2013.01)

(58) Field of Classification Search
   CPC . A61B 8/461; G01S 7/52039; G01S 7/52057; G01S 15/8963
   USPC .......................................................... 600/458
   See application file for complete search history.

(56) References Cited

U.S. PATENT DOCUMENTS

| | | | |
|---|---|---|---|
| 5,706,819 | A | 1/1998 | Hwang et al. |
| 6,014,473 | A * | 1/2000 | Hossack et al. ............... 382/294 |
| 6,454,714 | B1 * | 9/2002 | Ng .......................... A61B 8/06 600/443 |
| 7,302,850 | B2 | 12/2007 | Kamiyama |
| 7,583,857 | B2 | 9/2009 | Xu et al. |
| 7,886,603 | B2 | 2/2011 | Kamiyama |
| 2001/0034485 | A1 * | 10/2001 | Kawagishi .......... G01S 15/8963 600/443 |
| 2004/0215076 | A1 | 10/2004 | Kamiyama |
| 2007/0047840 | A1 | 3/2007 | Xu et al. |
| 2008/0058646 | A1 | 3/2008 | Kamiyama |
| 2008/0262354 | A1 | 10/2008 | Yoshida et al. |
| 2009/0177087 | A1 | 7/2009 | Kato et al. |
| 2011/0004097 | A1 | 1/2011 | Kamiyama |
| 2011/0075904 | A1 | 3/2011 | Yoshikawa et al. |
| 2012/0027282 | A1 | 2/2012 | Yoshikawa et al. |

FOREIGN PATENT DOCUMENTS

| | | |
|---|---|---|
| JP | 2006-247122 | 9/2006 |
| JP | 2007-054636 | 3/2007 |
| JP | 2007-330764 | 12/2007 |
| JP | 2009-005888 | 1/2009 |
| JP | 2009-082181 | 4/2009 |
| JP | 2010-099193 | 5/2010 |
| WO | 2007/080895 | 7/2007 |
| WO | 2009/110308 | 9/2009 |
| WO | 2010/117025 | 10/2010 |

OTHER PUBLICATIONS

Makiko Hayashi et al., "Correlation Between the Blood Supply and Grade of Malignancy of Hepatocellular Nodules Associated with Liver Cirrhosis: Evaluation by CT During Intraarterial Injection of Contrast Medium", AJR: 172, Apr. 1999, p. 969-976.

Hironori Tanaka et al., "New malignancy grading system for hepatocellular carcinoma using Sonazoid contrast enhanced ultrasonography", The Japan Society of Hepatology, Kanzo, vol. 50, No. 7, 2009, p. 397-399.

Japanese Office Action (and English translation thereof) dated Sep. 1, 2015, issued in Japanese Application No. 2012-534174.

* cited by examiner

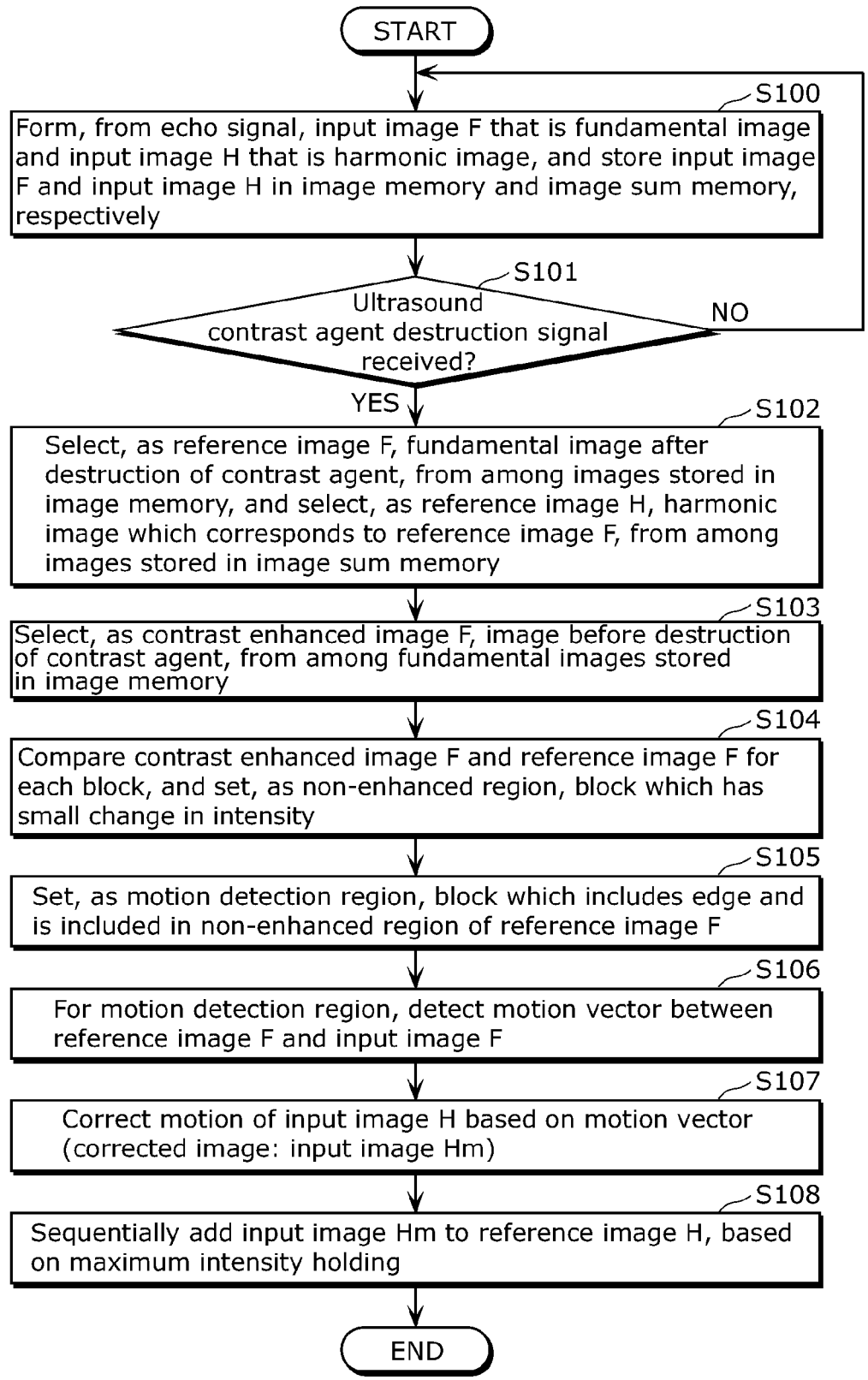

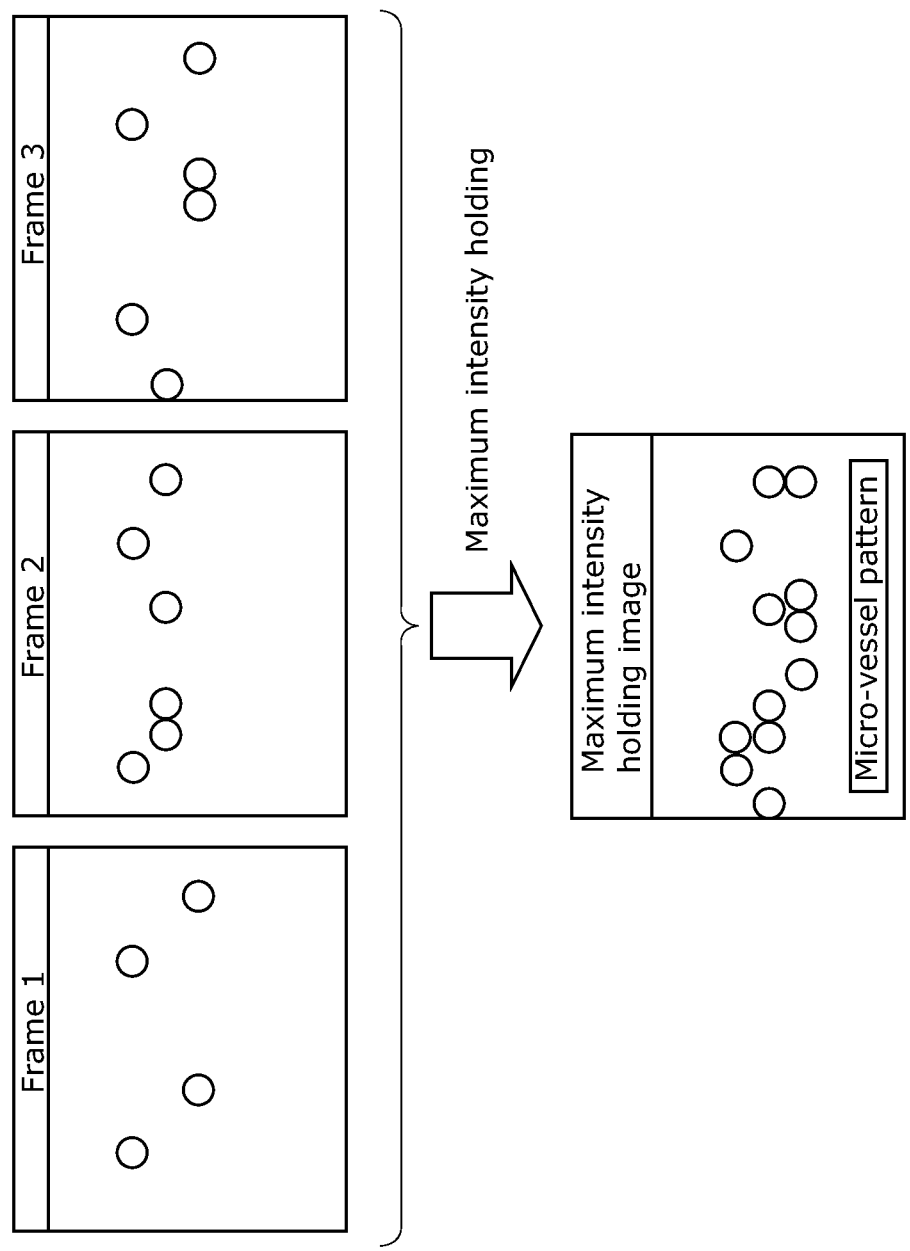

ULTRASOUND DIAGNOSTIC APPARATUS AND METHOD FOR OUTPUTTING ULTRASOUND DIAGNOSTIC IMAGE

CROSS REFERENCE TO RELATED APPLICATIONS

This is a continuation application of PCT International Application No. PCT/JP2012/001967 filed on Mar. 22, 2012, designating the United States of America, which is based on and claims priority of Japanese Patent Application No. 2011-083302 filed on Apr. 5, 2011. The entire disclosures of the above-identified applications, including the specifications, drawings and claims are incorporated herein by reference in their entirety.

FIELD

One or more exemplary embodiments disclosed herein relate generally to ultrasound diagnostic apparatuses, and methods for outputting an ultrasound diagnostic image, and particularly relates to an ultrasound diagnostic apparatus which outputs an ultrasound diagnostic image and a method for outputting an ultrasound diagnostic image of a subject to which an ultrasound contrast agent has been administered.

BACKGROUND

In recent years, contrast-enhanced ultrasonography has been conducted for benignancy and malignancy differentiation of a tumor. The contrast-enhanced ultrasonography is one of the image diagnosis methods for tumor characterization. The contrast-enhanced ultrasonography determines tumor grade by administering an ultrasound contrast agent having bubbles as a main component into the blood flow, and obtaining using an ultrasound diagnostic apparatus (for example, see FIG. 11) the images of the ultrasound contrast agent together with tissue of a subject as a video.

One of the analysis methods of tumor characterization is a diagnostic method based on a time intensity curve (TIC) shown in FIG. 6. The TIC is used to analyze a change in intensity over time observed in the site of interest. Research has been conducted for applying the TIC for malignancy grading of a tumor (Non-patent Literature 1).

Furthermore, recent years have seen studies for malignancy grading of a tumor based on a micro-vessel pattern in a tumor, by using the ultrasound contrast agent (Non-patent Literature 2). The micro-vessel pattern is represented as an image with a technique called a maximum intensity holding. As shown in FIG. 5, in the maximum intensity holding, each of bubbles of the ultrasound contrast agent passing through a microvessel appears on the image as a dot having high-intensity. The micro-vessel pattern is constructed by sequentially adding the intensities (Patent Literature 1). The maximum intensity holding is used in combination with destruction of the ultrasound contrast agent. Such a method is referred to as a flash replenishment imaging (FRI). In the FRI, ultrasound having a high sound pressure is transmitted to destroy the ultrasound contrast agent, and the ultrasound contrast agent flowing into the site of interest again is observed by a maximum intensity holding. With this, the flow of the ultrasound contrast agent can be repeatedly observed without administrating the ultrasound contrast agent to the subject again.

CITATION LIST

Patent Literature

[Patent Literature 1] Japanese Unexamined Patent Application Publication No. 2006-247122
[Patent Literature 2] Japanese Unexamined Patent Application Publication No. 2009-005888
[Patent Literature 3] Japanese Unexamined Patent Application Publication No. 2009-82181
[Patent Literature 4] U.S. Pat. No. 5,632,277
[Patent Literature 5] U.S. Pat. No. 5,706,819
[Patent Literature 6] U.S. Pat. No. 5,577,505

Non Patent Literature

[Non Patent Literature 1] Correlation Between the Blood Supply and Grade of Malignancy of Hepatocellular Nodules Associated with Liver Cirrhosis: Evaluation by CT During Intraarterial Injection of Contrast Medium. AJR: 172, April 1999, pp. 969-976
[Non Patent Literature 2] New malignancy grading system for hepatocellular carcinoma using Sonazoid contrast enhanced ultrasonography, Kanzo vol. 50(7), 2009, pp. 397-399

SUMMARY

Technical Problem

One non-limiting and exemplary embodiment provides an ultrasound diagnostic apparatus and the like which can correct misalignment among images enhanced with ultrasound contrast agent.

Solution to Problem

In one general aspect, the techniques disclosed here feature an ultrasound diagnostic apparatus which outputs an ultrasound diagnostic image of a subject to which an ultrasound contrast agent has been administered, the ultrasound diagnostic apparatus includes: an imaging unit configured to form images each of which corresponds to one of echo signals received from the subject; a motion detection region setting unit configured to select a first image from among images which include images of the ultrasound contrast agent, select a second image from among images which do not include images of the ultrasound contrast agent, and set, as a motion detection region, a region in which an amount of image change between the first image and the second image is smaller than a predetermined amount, the images which include images of the ultrasound contrast agent and the images which do not include images of the ultrasound contrast agent being included in the images formed by the imaging unit; and an output unit configured to output, as the ultrasound diagnostic image, the second image on which a position adjustment has been performed to match a position of the motion detection region set by the motion detection region setting unit and a position of a region included in the second image and similar in an image feature to the motion detection region.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

According to an ultrasound diagnostic apparatus and a method for outputting ultrasound diagnostic image disclosed in one or more exemplary embodiments or features, an image including a small amount of ultrasound contrast agent and an image including a great amount of ultrasound contrast agent are compared, and an image having a relatively small enhancement is selected to be set as a motion detection region. This makes it possible to correctly detect a motion even under the influence of contrast agent, and a misalignment between images can be removed by correction.

BRIEF DESCRIPTION OF DRAWINGS

These and other advantages and features will become apparent from the following description thereof taken in conjunction with the accompanying Drawings, by way of non-limiting examples of embodiments disclosed herein.

FIG. 2A is a flowchart according to Embodiment 1.

FIG. 5 is a diagram for describing a maximum intensity holding.

Figure 1:
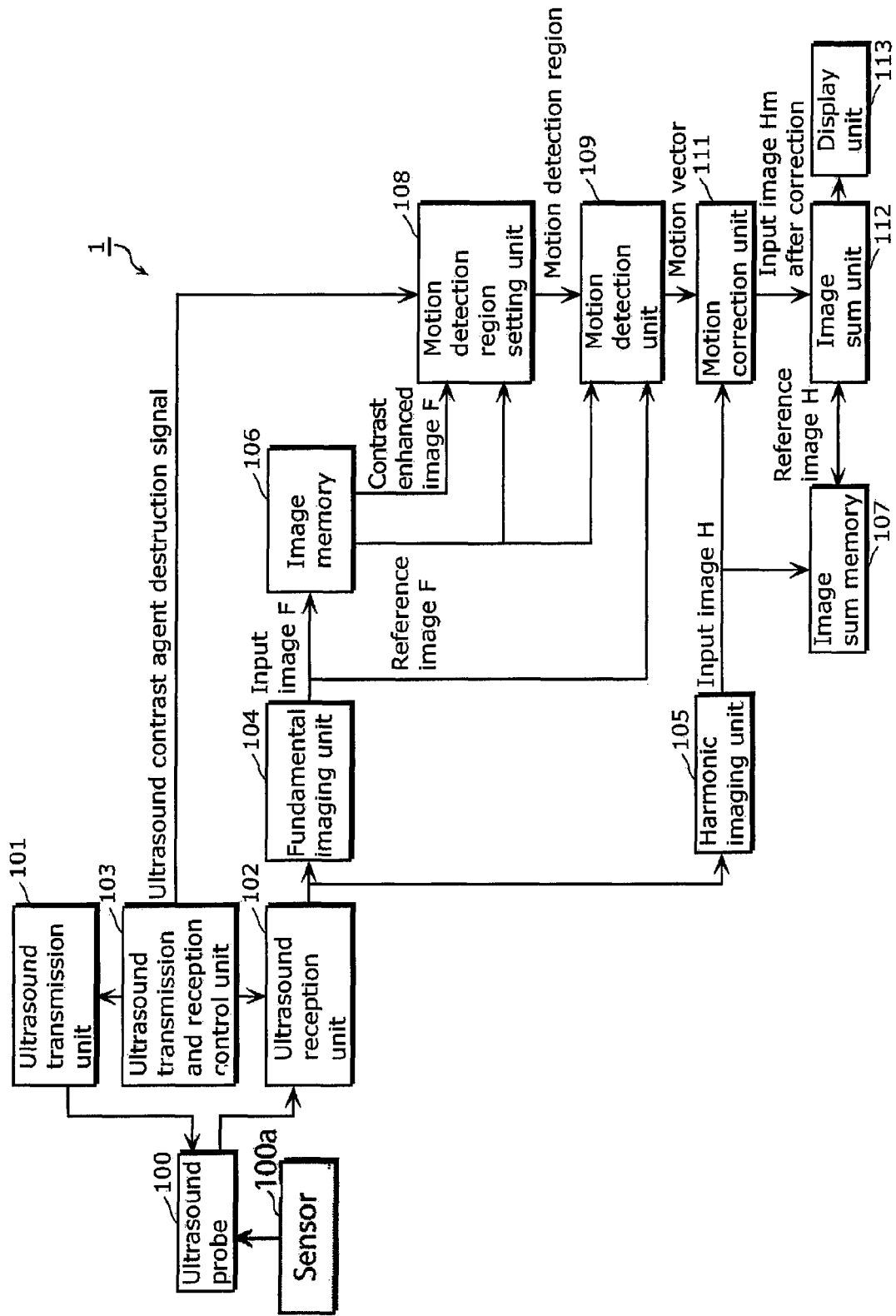
FIG. 1 is a configuration diagram of an ultrasound diagnostic apparatus according to Embodiment 1.

DESCRIPTION OF EMBODIMENTS (Underlying Knowledge Forming Basis of the Present Disclosure)

In relation to the method of tracking the site of interest disclosed in the Background section, the inventors have found the following problem.

According to a diagnostic method based on the TIC or the FRI, the site of interest is tracked across a plurality of images or the site of interest is tracked using an image obtained by sequentially summing a plurality of images. However, in any of the above diagnostic methods, the tracking of the site of interest is difficult when misalignment occurs between images due to a body motion of a subject or the like. Typically, the misalignment between the images is corrected by detecting a motion vector, which corresponds to the amount of misalignment, using a technique of pattern matching or the like. However, in the case of the contrast-enhanced ultrasonography, intensity pattern of the site of interest can be dynamically changed due to enhancement by the ultrasound contrast agent. In such cases, a corresponding pattern does not exist in each of the images. Thus, the site of interest can not be correctly tracked, which is a problem.

Due to this problem, there is an issue of correction of misalignment among images enhanced with the ultrasound contrast agent.

In view of this issue, according to the conventional technique described in Patent Literatures (PTLs) 1 to 3, motion detection is performed using a fundamental image which includes relatively small amount of images of the ultrasound contrast agent. However, in such cases, there are cases where the images of the ultrasound contrast agent are present in the fundamental image, and thus the effect of contrast enhancement cannot be fully avoided.

Furthermore, to make a diagnosis off-line based on the TIC, a fundamental image is necessary. However, only harmonic images are recorded in many cases, in consideration of capacity of a record server.

One non-limiting and exemplary embodiment provides an ultrasound diagnostic apparatus and the like which can correct the misalignment that occurs among the images enhanced with the ultrasound contrast agent.

According to an exemplary embodiment disclosed herein, an ultrasound diagnostic apparatus outputs an ultrasound diagnostic image of a subject to which an ultrasound contrast agent has been administered, the ultrasound diagnostic apparatus includes: an imaging unit configured to form images each of which corresponds to one of echo signals received from the subject; a motion detection region setting unit configured to select a first image from among images which include images of the ultrasound contrast agent, select a second image from among images which do not include images of the ultrasound contrast agent, and set, as a motion detection region, a region in which an amount of image change between the first image and the second image is smaller than a predetermined amount, the images which include images of the ultrasound contrast agent and the images which do not include images of the ultrasound contrast agent being included in the images formed by the imaging unit; and an output unit configured to output, as the ultrasound diagnostic image, the second image on which a position adjustment has been performed to match a position of the motion detection region set by the motion detection region setting unit and a position of a region included in the second image and similar in an image feature to the motion detection region.

With this, the ultrasound diagnostic apparatus can select, as the motion detection region, a region which is displayed at the same intensity in the first image and the second image irrespective of presence or absence of contrast enhancement by the ultrasound contrast agent, and includes a distinctive portion of the image. As described, the ultrasound diagnostic apparatus sets the motion detection region, adjusts the positions of the images based on the distinctive portion of the images, and thus can correct the misalignment that occurs among the images enhanced with the ultrasound contrast agent.

For example, when the selected second image includes more than one second image, the output unit is configured to output, as the ultrasound diagnostic image, an image obtained by summing the second images on which the position adjustment has been performed.

With this, it is possible to adjust positions of contrast enhanced images (second images) using the above-described motion detection region. In addition, by summing intensity values of the corresponding pixels in each of the second images on which the position adjustment has been performed, it is possible to obtain, as the ultrasound diagnostic image, a path of the ultrasound contrast agent useful for making a diagnosis.

For example, the motion detection region setting unit is configured to select the first image from among images which include images of the ultrasound contrast agent, select the second image from among images which do not include images of the ultrasound contrast agent, to set the motion detection region, the images which include images of the ultrasound contrast agent and the images which do not include images of the ultrasound contrast agent being included in the images formed by the imaging unit.

With this, as the first image and the second image, an image which is obtained after the ultrasound contrast agent is destroyed and is objectively believed as not being enhanced with the contrast agent, and an image which is obtained before the ultrasound contrast agent is destroyed and is objectively believed as being enhanced with the contrast agent are selected. Thus, the ultrasound diagnostic apparatus can correct more reliably the misalignment which occurs among the images enhanced with the ultrasound contrast agent.

For example, the ultrasound diagnostic apparatus further includes an ultrasound probe which transmits ultrasound to the subject, wherein the motion detection region setting unit is configured to select, as the first image, an image formed at a point in time before the ultrasound contrast agent is destroyed through generation of ultrasound having a high sound pressure by the ultrasound probe, and select, as the second image, an image formed at a point in time after the ultrasound contrast agent has been destroyed, to set the motion detection region.

With this, as the first image and the second image, an image which is obtained after flashing and is objectively believed as not being enhanced with the contrast agent, and an image which is obtained before flashing and is objectively believed as being enhanced with the contrast agent are selected. Here, the "flashing" is performed to destroy the contrast agent with ultrasound having a high sound pressure. Thus, the ultrasound diagnostic apparatus can correct more reliably the misalignment which occurs among the images enhanced with the ultrasound contrast agent.

For example, the ultrasound diagnostic apparatus further includes an ultrasound probe which transmits ultrasound to the subject, wherein the motion detection region setting unit is configured to select, as the first image, an image formed at a point in time immediately before the ultrasound contrast agent is destroyed through generation of ultrasound having a high sound pressure by the ultrasound probe, and select, as the second image, an image formed at a point in time immediately after the ultrasound contrast agent has been destroyed, to set the motion detection region.

With this, as the first image and the second image, an image which is obtained immediately after the destruction of the ultrasound contrast agent and is objectively believed as not being enhanced with the contrast agent, and an image which is obtained immediately before the destruction of the ultrasound contrast agent and is objectively believed as being enhanced with the contrast agent are selected. Thus, the ultrasound diagnostic apparatus can correct more reliably the misalignment which occurs among the images enhanced with the ultrasound contrast agent.

For example, the motion detection region setting unit is configured to select the first image and the second image to obtain a biggest difference between an average intensity of the first image and an average intensity of the second image, to set the motion detection region.

With this, as the first image and the second image, an image which is objectively believed to have a smallest enhancement by the contrast agent and an image which is objectively believed to have a strongest enhancement by the ultrasound contrast agent are selected. Thus, the ultrasound diagnostic apparatus can correct more reliably the misalignment which occurs among the images enhanced with the ultrasound contrast agent.

For example, the ultrasound diagnostic apparatus further includes: an ultrasound probe which receives the echo signals obtained from the subject; and a sensor which measures a position or an angle of the ultrasound probe relative to the subject, when the ultrasound probe receives each of the echo signals, wherein the motion detection region setting unit is configured to select the first image and the second image to obtain a difference smaller than or equal to a predetermined value between a value measured by the sensor when the first image is formed and a value measured by the sensor when the second image is formed, to set the motion detection region.

With this, it is more certain that the first image and the second image are the ultrasound diagnostic images which capture, at the same angle, the same site of the subject. Thus, the ultrasound diagnostic apparatus can correct more reliably the misalignment which occurs among the images enhanced with the ultrasound contrast agent.

For example, the motion detection region setting unit is configured to select, as one of the first image and the second image, an image which is among the images and has an average intensity greater than or equal to a predetermined value, and select, as the other of the first image and the second image, an image which is among the images and has an average intensity smaller than or equal to the predetermined value, to set the motion detection region.

With this, as the first image and the second image, an image which is objectively believed to have a relatively small enhancement by the contrast agent and an image which is objectively believed to have a relatively strong enhancement by the contrast agent are selected. Thus, the ultrasound diagnostic apparatus can correct more reliably the misalignment which occurs among the images enhanced with the ultrasound contrast agent.

For example, the ultrasound diagnostic apparatus further includes an enhancement determination unit configured to determine whether or not a difference between an average intensity of the motion detection region in the first image and an average intensity of a region which is in the second image and corresponds to the motion detection region is greater than a predetermined value, wherein, when the enhancement determination unit determines that the difference in the average intensity is greater than the predetermined value, the motion detection region setting unit is configured to reset the motion detection region.

With this, when a contrast enhancement appears in a region which is objectively believed to have a small enhancement and set as a region used for the position adjustment, it is possible to reset a region to be used for the position adjustment thereafter and continue the obtainment of the ultrasound diagnostic image.

For example, when the enhancement determination unit determines that the difference in the average intensity is greater than the predetermined value, the motion detection region setting unit is configured to reset the motion detection region by setting, to a new motion detection region, a region which includes the motion detection region.

With this, when a contrast enhancement appears in a region which is objectively believed to have a small enhancement and set as a region used for the position adjustment, it is possible to increase a size of the region used for the position adjustment and accurately detect the feature of the image for the position adjustment.

For example, the imaging unit is configured to form an image from a fundamental component and an image from a harmonic component, the fundamental component and the harmonic component being included in each of the echo signals received from the subject, and the motion detection region setting unit is configured to select the first image and the second image from among images each of which is the image formed from the harmonic component by the imaging unit, to set the motion detection region.

With this, the ultrasound diagnostic apparatus can output, as the ultrasound diagnostic image, an image which is formed from the harmonic component that clearly captures the image of the ultrasound contrast agent. Furthermore, when a diagnosis is made off-line, the fundamental image is not necessary, and thus it is possible to reduce the capacity load of the record server.

For example, the imaging unit is configured to form an image from a fundamental component and an image from a harmonic component, the fundamental component and the harmonic component being included in each of the echo signals received from the subject, and the motion detection region setting unit is configured to select the first image from among images each of which is the image formed from the fundamental component by the imaging unit, and select the second image from among images each of which is the image formed from the fundamental component or the image formed from the harmonic component by the imaging unit, to set the motion detection region.

With this, it is possible to set the region used for the position adjustment based on the image formed from the fundamental component that is relatively less likely to capture the image of the ultrasound contrast agent, and adjust position of the image which is formed from the harmonic component that corresponds to the image formed from the fundamental component. In addition, the positions of the images formed from the harmonic components are adjusted, and intensity values of the corresponding pixels are summed. Thus, the path of the ultrasound contrast agent useful for making a diagnosis is obtained as the ultrasound diagnostic image.

For example, the motion detection region setting unit is configured to determine, from among regions which are included in the first image and each include sub-regions, a region having a largest intensity gradient, and set, as the motion detection region, the region having the largest intensity gradient which is a region in which a difference in average intensity of each of the sub-regions is largest.

With this, a region which includes both a portion having high intensity and a portion having low intensity can be set as a region used for the position adjustment. It is possible to more accurately perform position adjustment, by using a point having a distinctive pattern of change in intensity in the region having both the portion having high intensity and the portion having low intensity.

For example, the ultrasonic diagnostic apparatus further includes: an ultrasound probe which transmits ultrasound and receives the echo signals; and an ultrasound transmission and reception control unit configured to control the transmission of the ultrasound and the reception of the echo signals performed by the ultrasound probe, wherein the ultrasound transmission and reception control unit is configured to cause the ultrasound probe to generate ultrasound having a high sound pressure, when a reception strength of an echo signal included in the echo signals received by the ultrasound probe is greater than or equal to a threshold value.

With this, when the amount of image of the contrast agent in the ultrasound diagnostic image formed by an echo signal exceeds the threshold value, the ultrasound diagnostic apparatus can automatically destroy the ultrasound contrast agent and obtain a path of the ultrasound contrast agent when a new ultrasound contrast agent flows in from a different site in the body of the subject. Thus, the operator of the ultrasound diagnostic apparatus does not have to destroy the ultrasound contrast agent under their own judgment, but the ultrasound diagnostic apparatus can automatically obtain the path of the new ultrasound contrast agent.

For example, the ultrasonic diagnostic apparatus further includes: an ultrasound probe which transmits ultrasound and receives the echo signals; and an ultrasound transmission and reception control unit configured to control the transmission of the ultrasound and the reception of the echo signals performed by the ultrasound probe, wherein the ultrasound transmission and reception control unit is configured to cause the ultrasound probe to generate ultrasound having a high sound pressure, when an amount of increase in reception strength per unit time of an echo signal included in the echo signals received by the ultrasound probe is smaller than or equal to a threshold value.

With this, the ultrasound diagnostic apparatus can automatically destroy the ultrasound contrast agent to obtain a path of the ultrasound contrast agent flowing in from a different site of the body of the subject, when the rate of increase of an area of the image of the path of the ultrasound contrast agent becomes small in the ultrasound diagnostic image which is formed by an echo signal and shown on the display. Thus, the operator of the ultrasound diagnostic apparatus does not have to destroy the ultrasound contrast agent under their own judgment, but the ultrasound diagnostic apparatus can automatically obtain the path of the new ultrasound contrast agent.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Hereinafter, certain exemplary embodiments are described in greater detail with reference to the accompanying Drawings.

Each of the exemplary embodiments described below shows a general or specific example. The numerical values, shapes, materials, structural elements, the arrangement and connection of the structural elements, steps, the processing order of the steps etc. shown in the following exemplary embodiments are mere examples, and therefore do not limit the scope of the appended Claims and their equivalents. Therefore, among the structural elements in the following exemplary embodiments, structural elements not recited in any one of the independent claims are described as arbitrary structural elements.

The following describes, as an example, the case in which FRI is employed. It should be noted that the following can also be applied to the diagnostic method based on TIC.

The exemplary embodiments below describes an example in which an image including a small amount of image of the ultrasound contrast agent and an image including a great amount of image of the ultrasound contrast agent are used, to select a region which is less susceptible to contrast enhancement by the ultrasound contrast agent and has great intensity gradient, perform motion detection, and perform position adjustment on the image.

The exemplary embodiments below employ the FRI to observe the inflow of the ultrasound contrast agent. Specifically, a user destroys the ultrasound contrast agent with the ultrasound having a high sound pressure, after observing a display screen of the ultrasound diagnostic apparatus being enhanced with the ultrasound contrast agent.

The following describes a configuration and an operation of a system.

Embodiment 1

FIG. 1 is a configuration diagram of an ultrasound diagnostic apparatus 1 according to Embodiment 1.

As shown in FIG. 1, the ultrasound diagnostic apparatus 1 according to Embodiment 1 includes: an ultrasound probe 100, an ultrasound transmission unit 101, an ultrasound reception unit 102, an ultrasound transmission and reception control unit 103, a fundamental imaging unit 104, a harmonic imaging unit 105, an image memory 106, an image sum memory 107, a motion detection region setting unit 108, a motion detection unit 109, a motion correction unit 111, an image sum unit 112, and a display unit 113. It should be noted that the fundamental imaging unit 104 is an example of an imaging unit. Furthermore, the harmonic imaging unit 105 is another example of the imaging unit. Furthermore, the display unit 113 is an example of an output unit.

(Configuration)

The ultrasound probe 100 converts an electric signal output from the ultrasound transmission unit 101 into ultrasound, and transmits the ultrasound to a subject. In addition, the ultrasound probe 100 converts an echo signal reflected off the subject into an electric signal, and outputs the electric signal to the ultrasound reception unit 102.

The ultrasound transmission unit 101 generates an electric signal, which is a source of an ultrasound signal, and outputs the electric signal to the ultrasound probe 100.

The ultrasound reception unit 102 converts the echo signal output from the ultrasound probe 100 into a digital signal, and then outputs the digital signal to each of the fundamental imaging unit 104 and the harmonic imaging unit 105.

The ultrasound transmission and reception control unit 103 controls transmission of ultrasound performed by the ultrasound transmission unit 101, and the reception of ultrasound performed by the ultrasound reception unit 102. Furthermore, when causing the ultrasound transmission unit 101 to generate ultrasound having a high sound pressure, which is for destroying the ultrasound contrast agent, the ultrasound transmission and reception control unit 103 transmits an ultrasound contrast agent destruction signal to the motion detection region setting unit 108.

The fundamental imaging unit 104 extracts a fundamental component from the echo signal output from the ultrasound reception unit 102, and converts the fundamental component into an intensity signal to form a fundamental image. Then, the fundamental imaging unit 104 outputs, as an input image F, the formed fundamental image to each of the image memory 106 and the motion detection unit 109. It should be noted that the fundamental imaging unit 104 is an example of the imaging unit.

The harmonic imaging unit 105 extracts a harmonic component from the echo signal output from the ultrasound reception unit 102, and converts the harmonic component into an intensity signal to form a harmonic image. Then, the harmonic imaging unit 105 outputs, as an input image H, the formed harmonic image to each of the image sum memory 107 and the motion correction unit 111. It should be noted that the harmonic imaging unit 105 is an example of the imaging unit.

The motion detection region setting unit 108 selects, from among one or more of the fundamental images stored in the image memory 106, as an image pair, an contrast enhanced image F which includes great amount of images of the ultrasound contrast agent and a reference image F which includes a small amount of images of ultrasound contrast agent. Then, based on the selected image pair, the motion detection region setting unit 108 sets a motion detection region. The set motion detection region is output to the motion detection unit 109. It should be noted that the image pair corresponds to the first image and the second image.

Here, the motion detection region setting unit 108 may select, as the image pair, arbitrary images from among one or more of the images stored in the image memory 106.

The motion detection unit 109 detects, based on the motion detection region output from the motion detection region setting unit 108, the motion vector between the images of the reference image F selected by the motion detection region setting unit 108 and the input image F output from the fundamental imaging unit 104. The detected motion vector is output to the motion correction unit 111.

The motion correction unit 111 performs, based on the motion vector output from the motion detection unit 109, motion correction on the input image H output from the harmonic imaging unit 105. The corrected harmonic image Hm is output to the image sum unit 112.

The image sum unit 112 sequentially adds the input image Hm, which is output from the motion correction unit 111, to the reference image H stored in the image sum memory 107. At this time, the image sum unit 112 sums the images so that the biggest value is held in each dot, correspondingly. The summed image is output to the display unit 113.

The display unit 113 displays a summed image that is generated through the sequential summation of the input images Hm performed by the image sum unit 112. It should be noted that the display unit 113 is an example of the output unit.

The apparatus configuration according to Embodiment 1 is as described above.

(Operation)

The following describes, using FIG. 2A, a flow of operations performed in Embodiment 1.

FIG. 2A is a flowchart according to Embodiment 1.

[Step S100]

Figure 7:
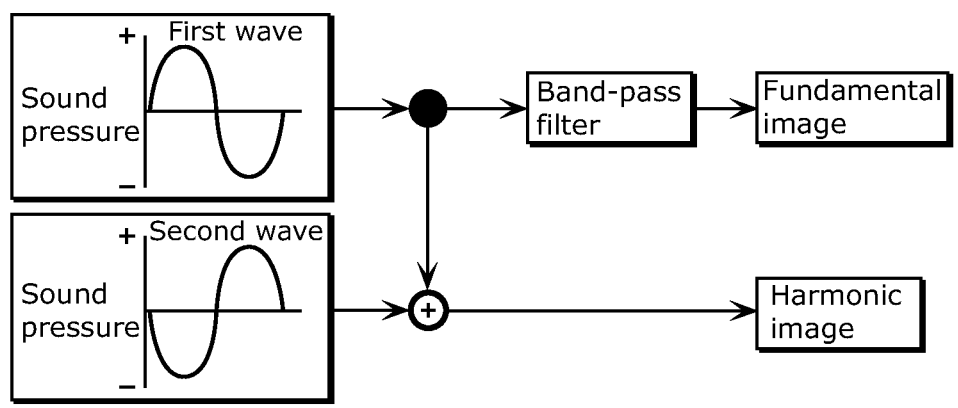
FIG. 7 is a diagram for describing an extraction of a fundamental and harmonic component in a pulse inversion method.

First, the fundamental imaging unit 104 extracts, using a filter, the fundamental component from an echo signal, and converts the fundamental component into the intensity signal to form the fundamental image F. On the other hand, the harmonic imaging unit 105 forms, with a double transmission rate method such as a pulse inversion imaging (PTLs 4 and 5) or an amplitude modulation imaging (PTL 6), the input image H which is formed from the harmonic component. At this time, as shown in FIG. 7, the fundamental imaging unit 104 forms the fundamental image from one of the echo signals transmitted twice. Next, the fundamental imaging unit 104 stores the input image F in the image memory 106, and the harmonic imaging unit 105 stores the input image H in the image sum memory 107. Furthermore, the fundamental imaging unit 104 outputs the input image F to the motion detection unit 109, and the harmonic imaging unit 105 outputs the input image H to the motion correction unit 111.

[Step S101]

Next, the motion detection region setting unit 108 transits to a waiting state waiting for an operation, which is for destroying the ultrasound contrast agent, performed by a user. When the user does not perform the operation, the motion detection region setting unit 108 returns to Step S100 to generate an image from the next echo signal.

[Step S102]

When the destruction control signal is received, the motion detection region setting unit 108 selects, as the reference image F, an image obtained immediately after the destruction of the ultrasound contrast agent, from among one or more of the fundamental images stored in the image memory 106. The reference image F includes a small amount of ultrasound contrast agent and is the fundamental image which corresponds to an initial image used in an after-mentioned maximum intensity holding. Furthermore, the motion detection region setting unit 108 selects, as the reference image H, the harmonic image which corresponds to the reference image F, from among one or more of the images stored in the image sum memory 107.

[Step S103]

Next, the motion detection region setting unit 108 selects, as the contrast enhanced image F, an image immediately before the destruction of the ultrasound contrast agent, from among one or more of the fundamental images stored in the image memory 106. The contrast enhanced image F is an image which is obtained with the ultrasound probe at the same position as when the reference image F is obtained. It should be noted that, in this embodiment, it is assumed that the period of time required to destroy the ultrasound contrast agent is short and the misalignment between the images is negligible.

[Step S104]

Next, the motion detection region setting unit 108 compares the reference image F and the contrast enhanced image F for each of the blocks included in the images, and set, as a non-enhanced region, the block having a small change in intensity between the images. The change in intensity is determined based on a difference of average intensity within a block, and set, as a non-enhanced region, the block which satisfies (Expression 1), where A represents an average intensity within the block after the destruction, B represents an average intensity within the block before the destruction, n represents the number of pixels within the block, and T represents a threshold value.

[Math. 1]

$$|A - B| < T, A = \sum_{i=1}^{n} A_i/n, B = \sum_{i=1}^{n} B_i/n \quad \text{(Expression 1)}$$

Here, the threshold value T is set to a value which corresponds to 10% of the dynamic range of an image.

[Step S105]

Next, the motion detection region setting unit 108 determines whether an edge is present in the non-enhanced region which is set. A specific method for the determination is described below. Each block is divided into subblocks, and the average intensity is calculated for each of the subblocks. After calculating the difference of average intensity between the subblocks, a biggest value of difference between the average intensity of each of the subblocks is determined as the edge value of the block. Specifically, a block is divided into subblocks of p, q, r, and s, and a block which satisfies (Expression 2) is set as the motion detection region, where P, Q, R, and S represents an average intensity of p, q, r, and s, respectively, n represents the number of pixels of each of the subblocks, and T represents a threshold value.

[Math. 2]

$$\text{MAX}(|P - Q|, |R - S|, |P - R|, |Q - S|) < T, \quad \text{(Expression 2)}$$

$$P = \sum_{i=1}^{n} P_i/n, Q = \sum_{i=1}^{n} Q_i/n, R = \sum_{i=1}^{n} R_i/n, S = \sum_{i=1}^{n} S_i/n$$

Here, the threshold value T is set to, for example, a value that is 50% of the dynamic range of an image.

[Step S106]

Next, the motion detection unit 109 detects a motion vector between the reference image F and the input image F. As a method of detecting the motion vector, it is possible to apply, for the motion detection region that is set for the reference image F, a method in which a conventional pattern matching is performed to obtain the motion vector.

[Step S107]

Figure 8A:
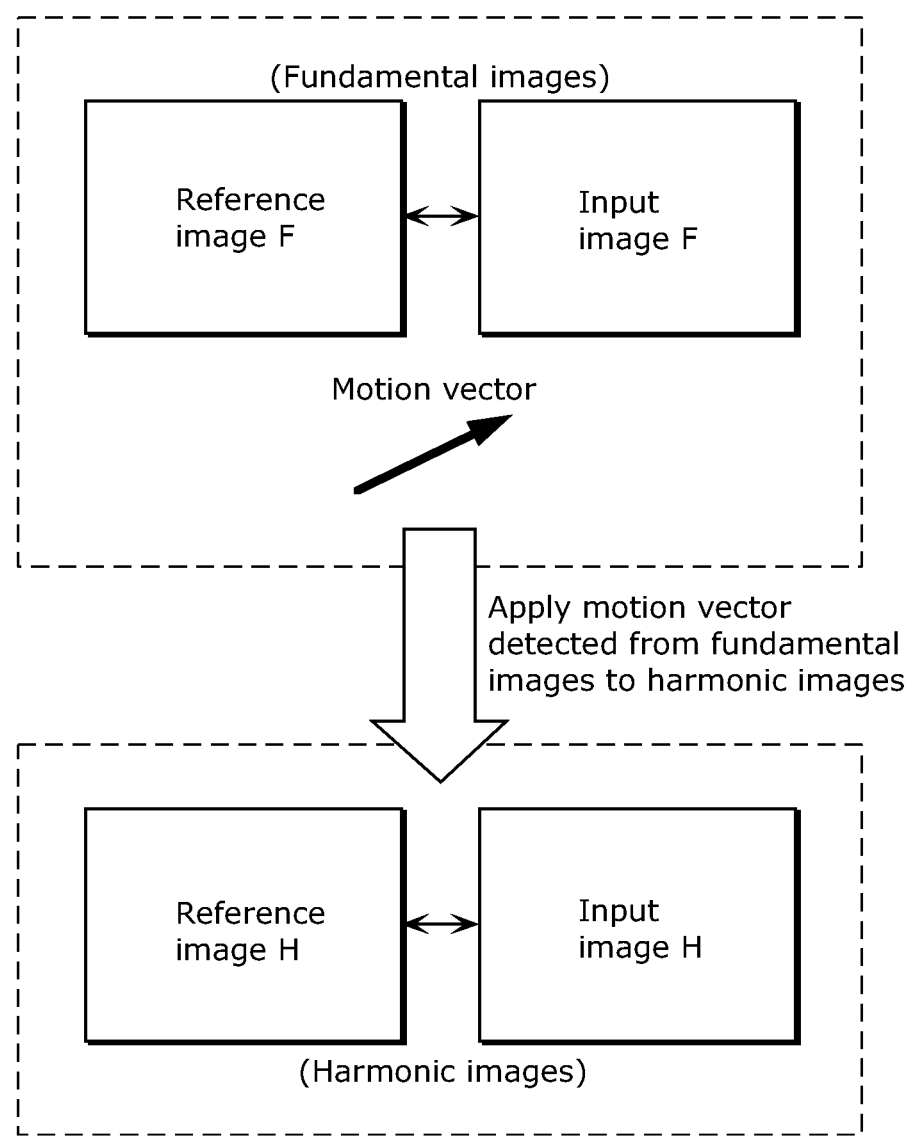
FIG. 8A is a diagram for describing how a motion vector detected from a fundamental image is used.

Next, the motion correction unit 111 corrects misalignment of the input image F with respect to the reference image F by translation. As shown in FIG. 8A, the target of the motion correction is the input image H of the harmonic image, not of the fundamental image. When correcting a global motion such as when a translation is performed on the entire image, the amount of correction is determined to be an average value or a median value of the motion vectors obtained in the motion detection regions. On the other hand, when correcting a local motion in a unit of region (at minimum, in a unit of a pixel), a motion vector of each region is determined by interpolation.

[Step S108]

Lastly, the image sum unit 112 constructs a blood stream pattern from the harmonic image with maximum intensity holding. Specifically, the image sum unit 112 sequentially adds the input image Hm to the reference image H which is stored in the image sum memory 107. The image generated as a result of the summation is output as the ultrasound diagnostic image.

The operation performed in this Embodiment is as described above.

It should be noted that, when selecting the image pair from among the images stored in the image memory 106, for example, the following may be performed to allow the motion detection using the motion detection region to be more effective.

An image which includes great amount of images of the ultrasound contrast agent and an image which does not include an image of the ultrasound contrast agent may be selected as the image pair.

When a flashing, that is, the destruction of the ultrasound contrast agent in the subject body through generation of ultrasound having a high sound pressure by the ultrasound probe is performed, an image which is obtained at the point in time before the flashing is performed and an image which is obtained at the point in time after the flashing may be selected as the image pair.

Furthermore, when a flashing, that is, the destruction of the ultrasound contrast agent in the subject body through generation of ultrasound having a high sound pressure by the ultrasound probe is performed, an image which is obtained at the point in time immediately before the flashing is performed and an image which is obtained at the point in time immediately after the flashing may be selected as the image pair.

Furthermore, two pictures between which the difference in average intensity of the image is the biggest may be selected as the image pair.

Furthermore, when the ultrasound probe includes a sensor 100a for measuring a position or an angle, two images may be selected as the image pair so that the difference between the measurement value of one image and the measurement value of the other image obtained by the sensor does not exceed a threshold value.

Furthermore, an image of which average intensity is greater than or equal to a predetermined value and an image of which average intensity is different and smaller than or equal to the predetermined value may be selected as the image pair.

(Effect)

Figure 8B:
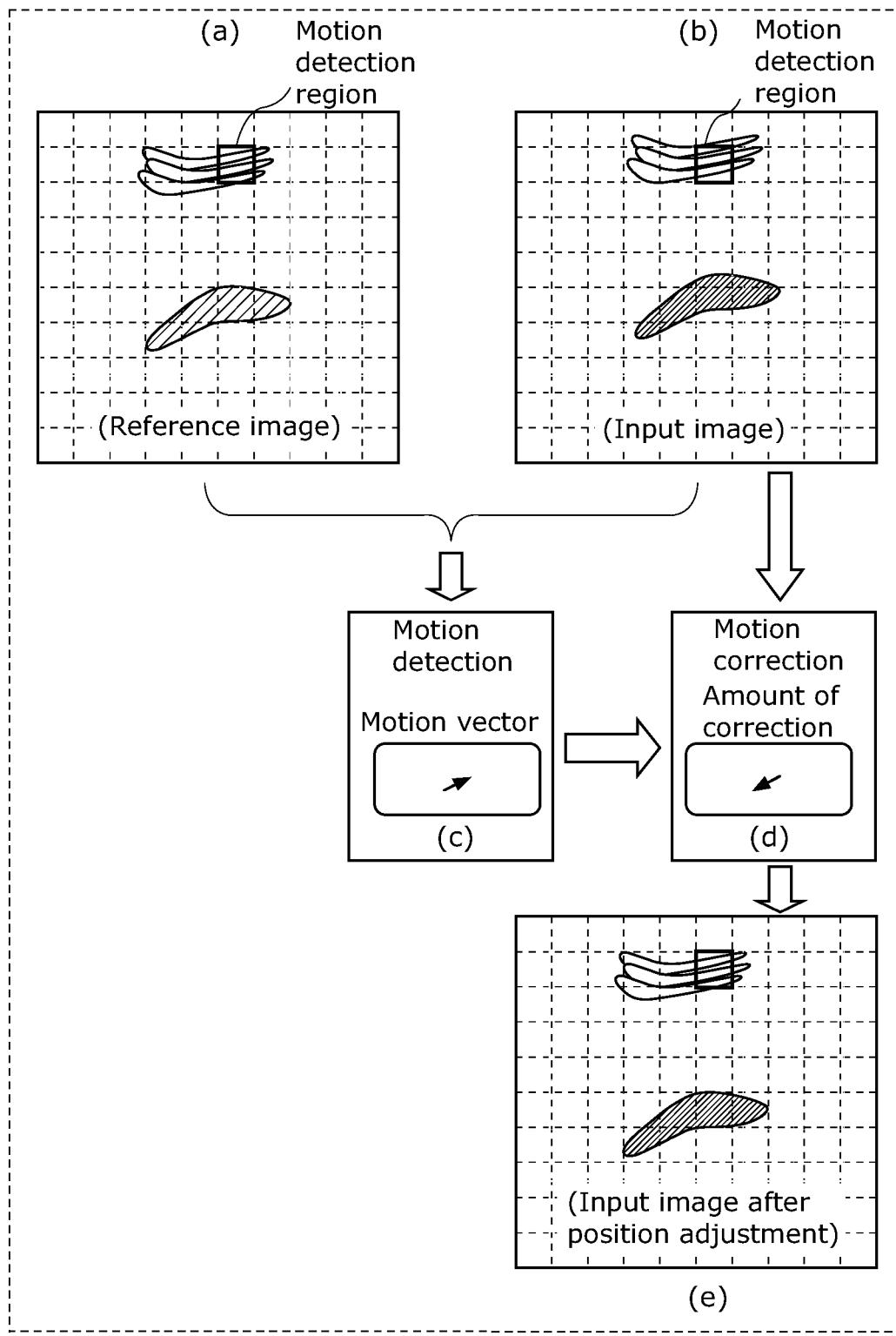
FIG. 8B is a conceptual diagram showing position adjustment using the motion vector performed on an input image.

FIG. 8B is a conceptual diagram showing a position adjustment using a motion vector performed on the input image.

As shown in FIG. 8B, according to this embodiment, an image (a) which includes the images of the ultrasound contrast agent in a small amount and an image (b) which includes the images of the ultrasound contrast agent in a great amount are selected, and pattern similarity between the images is evaluated for each of the regions included in the images, and each of the regions thereby can be classified into an enhanced region or a non-enhanced region. It is possible to set, as a motion detection region, from among the non-enhanced regions, a region having a large intensity gradient, realize the motion detection (calculate motion vector (c)), and perform position adjustment (d) and (e) on the image. Furthermore, the above-described operation can be realized with a similar operation procedure as with the conventional FRI.

Furthermore, an image including the images of the ultrasound contrast agent in a great amount obtained before the destruction of the ultrasound contrast agent and an image including the images of the ultrasound contrast agent in a small amount obtained after the destruction of the ultrasound contrast agent, and an image obtained after an elapse of a predetermined period of time since the destruction of the ultrasound contrast agent are selected, and pattern similarity between the images are evaluated for each of the regions included in the images, and thereby each region can be classified into an enhanced region or a non-enhanced region. With this, it is possible to realize a motion detection from which a contrast enhanced region is removed, and perform position adjustment on the image obtained after an elapse of a predetermined period of time since the destruction of the ultrasound contrast agent. Furthermore, the above-described operation can be implemented with a similar operation procedure as with the conventional FRI.

As described, according to an exemplary embodiment disclosed herein, the ultrasound diagnostic apparatus can select, as the motion detection region, a region which is displayed at the same intensity in the first image and the second image irrespective of presence or absence of contrast enhancement by the ultrasound contrast agent, and includes a distinctive portion of the image. As described, the ultrasound diagnostic apparatus sets the motion detection region, adjusts the positions of the images based on the distinctive portion of the images, and thus can correct misalignment that occurs among the images enhanced with the ultrasound contrast agent.

Furthermore, it is possible to adjust positions of contrast enhanced images (second images) using the above-described motion detection region. In addition, by summing intensity values of the corresponding pixels in each of the second images on which the position adjustment has been performed, it is possible to obtain, as the ultrasound diagnostic image, a path of the ultrasound contrast agent useful for making a diagnosis.

Furthermore, as the first image and the second image, an image which is obtained after the ultrasound contrast agent is destroyed and is objectively believed as not being enhanced with the contrast agent, and an image which is obtained before the ultrasound contrast agent is destroyed and is objectively believed as being enhanced with the contrast agent are selected. Thus, the ultrasound diagnostic apparatus can correct more reliably the misalignment which occurs among the images enhanced with the ultrasound contrast agent.

Furthermore, as the first image and the second image, an image which is obtained after flashing and is objectively believed as not being enhanced with the contrast agent, and an image which is obtained before flashing and is objectively believed as being enhanced with the contrast agent are selected. Here, the "flashing" is performed to destroy the contrast agent with ultrasound having a high sound pressure. Thus, the ultrasound diagnostic apparatus can correct more reliably the misalignment which occurs among the images enhanced with the ultrasound contrast agent.

Furthermore, as the first image and the second image, an image which is obtained immediately after the destruction of the ultrasound contrast agent and is objectively believed as not being enhanced with the contrast agent, and an image which is obtained immediately before the destruction of the ultrasound contrast agent and is objectively believed as being enhanced with the contrast agent are selected. Thus, the ultrasound diagnostic apparatus can correct more reliably the misalignment which occurs among the images enhanced with the ultrasound contrast agent.

Furthermore, as the first image and the second image, an image which is objectively believed to have a smallest enhancement by the contrast agent and an image which is objectively believed to have a greatest enhancement by the ultrasound contrast agent are selected. Thus, the ultrasound diagnostic apparatus can correct more reliably the misalignment which occurs among the images enhanced with the ultrasound contrast agent.

Furthermore, it is more certain that the first image and the second image are the ultrasound diagnostic images which capture, at the same angle, the same site of the subject. Thus, the ultrasound diagnostic apparatus can correct more reliably the misalignment which occurs among the images enhanced with the ultrasound contrast agent.

Furthermore, as the first image and the second image, an image which is objectively believed to have a relatively small enhancement by the contrast agent and an image which is objectively believed to have a relatively strong enhancement by the contrast agent are selected. Thus, the ultrasound diagnostic apparatus can correct more reliably the misalignment which occurs among the images enhanced with the ultrasound contrast agent.

It is possible to set the region used for the position adjustment based on the image formed from the fundamental component that is relatively less likely to capture the image of the ultrasound contrast agent, and adjust position of the image.

Furthermore, a region which includes both a portion having high intensity and a portion having low intensity can be set as a region used for the position adjustment. It is possible to more accurately perform position adjustment, by using a point having a distinctive pattern of change in intensity in the region having both the portion having high intensity and the portion having low intensity.

Variation 1 of Embodiment 1

Figure 9:
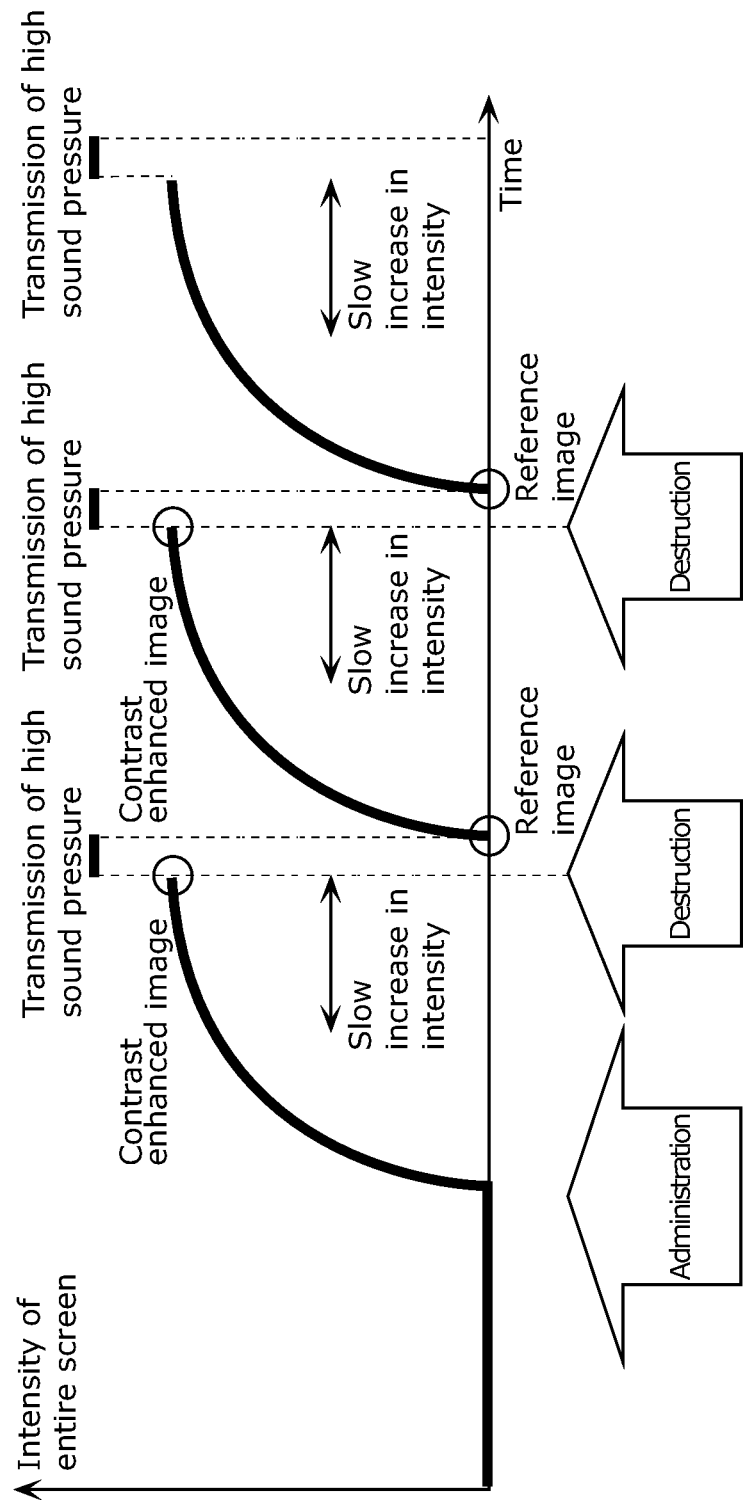
FIG. 9 is a diagram for describing a relationship between a destruction of an ultrasound contrast agent and a change in intensity.

In the above, the user destroys the ultrasound contrast agent, after observing a display being enhanced with the ultrasound contrast agent. However, the observation performed by the user may be automated. For example, as shown in FIG. 9, after the administration of the ultrasound contrast agent, intensity of the entire image may be observed in time sequence, and the ultrasound contrast agent may be destroyed at the time when the increase in intensity is slowed or when an intensity value becomes greater than or equal to a predetermined value.

Furthermore, when selecting the contrast enhanced image F and the reference image F, an image immediately before and an image immediately after the destruction of the ultrasound contrast agent are selected. However, as shown in FIG. 9, when the intensity of the entire image is observed in time sequence, images having a biggest difference in intensity, which are obtained before and after the destruction of the ultrasound contrast agent, may be selected as an image pair. With this, it is possible to select an image which includes the images of the ultrasound contrast agent in a great amount and an image which includes the images of the ultrasound contrast agent in a small amount.

Furthermore, when the contrast enhanced image F and the reference image F are selected, the images immediately before and after the destruction of the ultrasound contrast agent are selected, to obtain cross sections which are the same as much as possible. However, a position sensor 100a, such as a magnetic sensor or the like, may be attached to the ultrasound probe 100, and an image pair having the same cross sections may be selected.

Furthermore, the determination of a change in intensity in Step S105 is performed based on the difference in average intensity. However, the determination may be made based on pattern similarity. For example, sum-of-absolute difference (SAD) may be used. In this case, a block which satisfies (Expression 3) is set as a non-enhanced region, where A represents an image after the destruction of the ultrasound contrast agent, B represents an image before the destruction of the ultrasound contrast agent, n represents the number of pixels in a block, E represents an error, and T represents a threshold value.

[Math. 3]

$$E = \sum_{i=i}^{n} |A_i - B_i| < T \qquad \text{(Expression 3)}$$

Furthermore, each of the threshold value for (Expression 1) to (Expression 3) is set according to a ratio with respect to the dynamic range of the image. However, the threshold value is not limited to such an example but may be a fixed value.

Furthermore, the above described the operation in which motion is corrected in real-time. However, motion may be corrected off-line. In order to correct motion off-line, the ultrasound diagnostic apparatus stores the ultrasound contrast agent destruction control signal in association with an image in the memory, and reads and refers to the image and the signal. Furthermore, when the destruction control signal is not stored, the timing for destroying the ultrasound contrast agent may be determined based on intensity of the entire image. Specifically, when the ultrasound having a high sound pressure for destroying the ultrasound contrast agent is transmitted, as shown in FIG. 9, the intensity is usually saturated. Thus, the timing when the intensity of the entire image reaches the predetermined threshold value may be detected as the timing when the ultrasound contrast agent was destroyed.

Furthermore, although the above has been described with the example of the FRI, the above description can also be applied to a diagnostic method based on the TIC.

As described, according to an exemplary embodiment disclosed herein, when the amount of images of the contrast agent in the ultrasound diagnostic image formed by an echo signal exceeds the threshold value, the ultrasound diagnostic apparatus can automatically destroy the ultrasound contrast agent and obtain a path of the ultrasound contrast agent when a new ultrasound contrast agent flows in from a different site in the body of the subject. Thus, the operator of the ultrasound diagnostic apparatus does not have to destroy the ultrasound contrast agent under their own judgment, but the ultrasound diagnostic apparatus can automatically obtain the path of the new ultrasound contrast agent.

Furthermore, the ultrasound diagnostic apparatus can automatically destroy the ultrasound contrast agent to obtain a path of the ultrasound contrast agent flowing in from a different site of the body of the subject, when the rate of increase of an area of the image of the path of the ultrasound contrast agent becomes small in the ultrasound diagnostic image which is formed by an echo signal and shown on the display. Thus, the operator of the ultrasound diagnostic apparatus does not have to destroy the ultrasound contrast agent under their own judgment, but the ultrasound diagnostic apparatus can automatically obtain the path of the new ultrasound contrast agent.

Variation 2 of Embodiment 1

The following describes Variation 2 of Embodiment 1. This variation describes an example in which the position adjustment is performed using, from the fundamental image and the harmonic image formed from the echo signal obtained from the subject, the harmonic image.

Figure 2B:
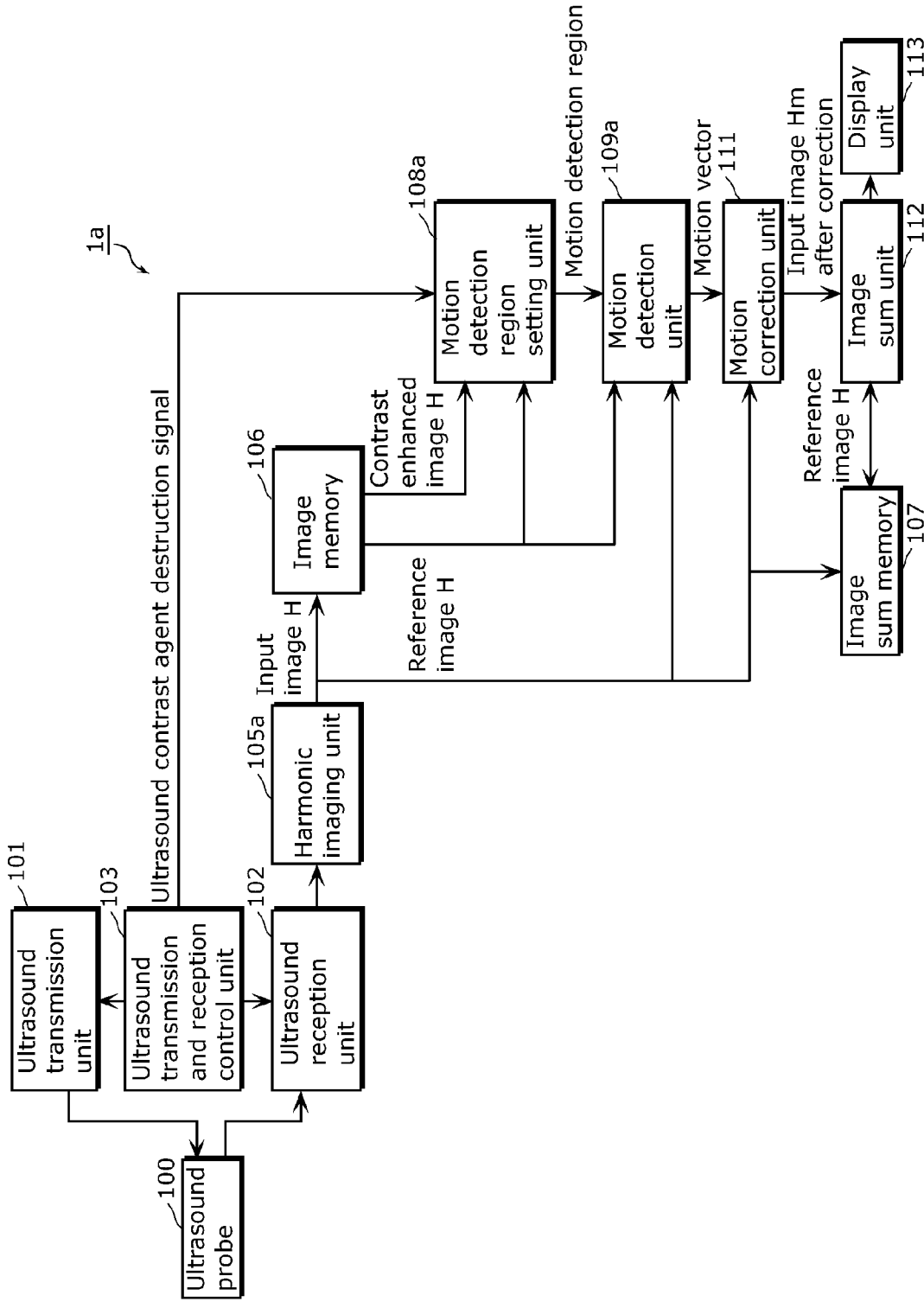
FIG. 2B is a configuration diagram of an ultrasound diagnostic apparatus according to Variation 2 of Embodiment 1.

FIG. 2B is an example of a configuration diagram of an ultrasound diagnostic apparatus 1a according to this variation.

As shown in FIG. 2B, the ultrasound diagnostic apparatus 1a according to this variation includes: the ultrasound probe 100, the ultrasound transmission unit 101, the ultrasound reception unit 102, the ultrasound transmission and reception control unit 103, a harmonic imaging unit 105a, an image memory 106a, the image sum memory 107, a motion detection region setting unit 108a, a motion detection unit 109a, the motion correction unit 111, the image sum unit 112 and the display unit 113. A significant difference between this variation and Embodiment 1 is that this variation does not include the fundamental imaging unit 104.

(Configuration)

The following describes only configuration blocks which are different from the configuration blocks in Embodiment 1.

The ultrasound reception unit 102 converts the echo signal output from the ultrasound probe 100 into a digital signal, and then outputs the digital signal to the harmonic imaging unit 105a.

The harmonic imaging unit 105a extracts a harmonic component from the echo signal output from the ultrasound reception unit 102, and converts the harmonic component into an intensity signal to form a harmonic image. Then, the harmonic imaging unit 105a outputs, as an input image H, the formed harmonic image to each of the image memory 106, the motion detection unit 109a, the image sum memory 107, and the motion correction unit 111.

The motion detection region setting unit 108a selects, as the image pair, from among the harmonic images stored in the image memory 106, a contrast enhanced image H including a great amount of images of the ultrasound contrast agent and a reference image H including a small amount of images of the ultrasound contrast agent. Then, based on the selected image pair, the motion detection region setting unit 108a sets a motion detection region. The set motion detection region is output to the motion detection unit 109a.

The motion detection unit 109a detects, based on the motion detection region output from the motion detection region setting unit 108a, the motion vector between the images of the reference image H selected by the motion detection region setting unit 108a and the input image H output from the harmonic imaging unit 105a. The detected motion vector is output to the motion correction unit 111.

Other function blocks are the same as those in Embodiment 1, and thus the descriptions thereof are omitted.

(Operation)

Figure 2C:
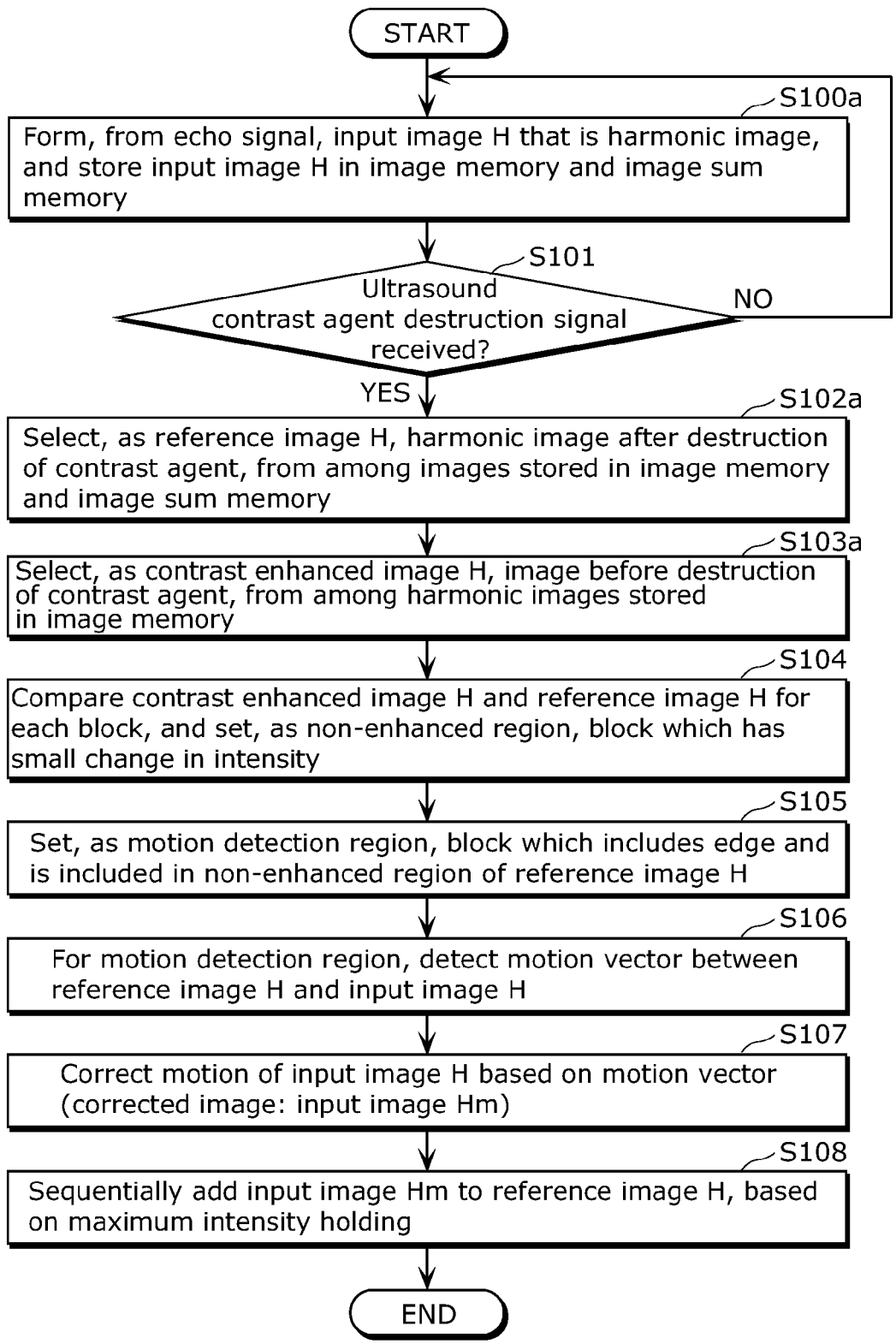
FIG. 2C is a flowchart according to Variation 2 of Embodiment 1.

FIG. 2C is a flowchart according to Variation 2 of this embodiment.

The following describes only operations which are different from the operations performed in Embodiment 1. In this variation, instead of Step S100 in Embodiment 1, Step 100a is executed. Furthermore, instead of Step S102, Step 102a is executed.

[Step S100a]

First, the harmonic imaging unit 105a forms the input image H which is formed from the harmonic component, with a double transmission rate method, such as a pulse inversion imaging or an amplitude modulation imaging. Next, the harmonic imaging unit 105a stores the input image H in each of the image memory 106 and the image sum memory 107. Furthermore, the harmonic imaging unit 105a outputs the input image H to each of the motion detection unit 109a and the motion correction unit 111.

[Step S102a]

When the destruction control signal is received, the motion detection region setting unit 108a selects, as the reference image H, an image immediately after the destruction of the ultrasound contrast agent, from among one or more of the harmonic images stored in each of the image memory 106 and the image sum memory 107. The reference image H includes a small amount of images of the ultrasound contrast agent, and is the fundamental image which corresponds to an initial image used in an after-mentioned maximum intensity holding.

[Step S103a]

Next, the motion detection region setting unit 108a selects, as the contrast enhanced image H, an image immediately before the destruction of the ultrasound contrast agent, from among one or more of the harmonic images stored in the image memory 106. The contrast enhanced image F is an image which is obtained with the ultrasound probe at the same position as when the reference image H is obtained. It should be noted that, in this variation, it is assumed that the period of time required to destroy the ultrasound contrast agent is short and the misalignment between the images is negligible.

The other operations are the same as those performed in Embodiment 1, except that the processing performed on the reference image F in Embodiment 1 is performed on the reference image H, and the processing performed on the input image F in Embodiment 1 is performed on the input image H.

According to this variation, the misalignment that occurs among the images enhanced with the ultrasound contrast agent can be corrected using, from the fundamental image and the harmonic image, the harmonic image.

It should be noted that this variation described an example in which the inflow of the ultrasound contrast agent is observed with the FRI. However, this variation can also be applied to the diagnostic method based on the TIC. When a diagnosis based on the TIC is made off-line, the fundamental image is not necessary, and thus it is possible to reduce the capacity load of the record server.

With this, according to the ultrasound diagnostic apparatus according to an exemplary embodiment disclosed herein, it is possible to output, as the ultrasound diagnostic image, an image which is formed from the harmonic component that clearly captures the image of the ultrasound contrast agent. Furthermore, when a diagnosis is made off-line, the fundamental image is not necessary, and thus it is possible to reduce the capacity load of the record server.

Embodiment 2

Figure 3:
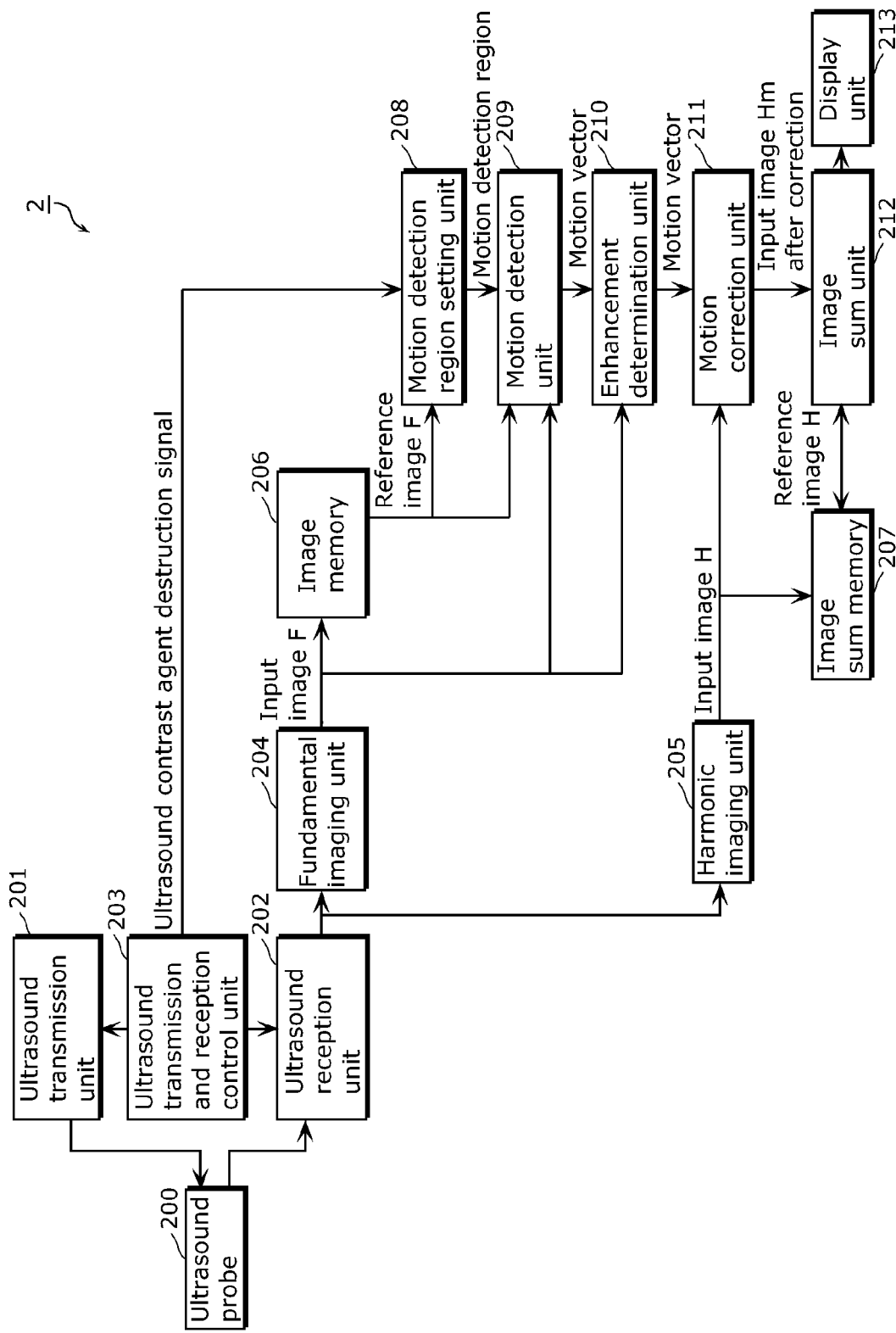
FIG. 3 is a configuration diagram of an ultrasound diagnostic apparatus according to Embodiment 2.

FIG. 3 is a configuration diagram of an ultrasound diagnostic apparatus 2 according to Embodiment 2.

As shown in FIG. 3, the ultrasound diagnostic apparatus 2 according to Embodiment 2 includes: an ultrasound probe 200, an ultrasound transmission unit 201, an ultrasound reception unit 202, an ultrasound transmission and reception control unit 203, a fundamental imaging unit 204, a harmonic imaging unit 205, an image memory 206, an image sum memory 207, a motion detection region setting unit 208, a motion detection unit 209, an enhancement determination unit 210, a motion correction unit 211, an image sum unit 212, and a display unit 213.

(Configuration)

The ultrasound probe 200, the ultrasound transmission unit 201, the ultrasound reception unit 202, and the ultrasound transmission and reception control unit 203 correspond respectively to the ultrasound probe 100, the ultrasound transmission unit 101, the ultrasound reception unit 102, and the ultrasound transmission and reception control unit 103 in Embodiment 1. Thus, the descriptions thereof are omitted.

The fundamental imaging unit 204 extracts a fundamental component of the echo signal output from the ultrasound reception unit 202, and converts the fundamental component into an intensity signal to form a fundamental image. Then, the fundamental imaging unit 204 outputs, as an input image F, the formed fundamental image to each of the image memory 206, the motion detection unit 209, and the enhancement determination unit 210.

The harmonic imaging unit 205 extracts a harmonic component of the echo signal output from the ultrasound reception unit 202, and converts the harmonic component into the intensity signal to form a harmonic image. Then, the harmonic imaging unit 205 outputs, as an input image H, the formed harmonic image to each of the image sum memory 207 and the motion correction unit 211.

The motion detection region setting unit 208 sets, for the reference image F stored in the image memory 206, a motion detection region. The set motion detection region is output to the motion detection unit 209.

The motion detection unit 209 detects, using the motion detection region output from the motion detection region setting unit 208, the motion vector between the two images of the reference image F selected by the motion detection region setting unit 208 and the input image F output from the fundamental imaging unit 204. The detected motion vector is output to the enhancement determination unit 210.

The enhancement determination unit 210 determines whether a contrast enhancement is present or absent in the referent of the motion vector output from the motion detection unit 209. When the referent is under the contrast enhancement the enhancement determination unit 210 invalidates the motion vector, and output, to the motion correction unit 211, only the motion vector in the region which is not under the contrast enhancement.

The processing performed by the motion correction unit 211, the image sum unit 212, and the display unit 213 are the same as those in Embodiment 1. Thus, the descriptions thereof are omitted.

The apparatus configuration according to Embodiment 2 is as described above.

(Operation)

Figure 4A:
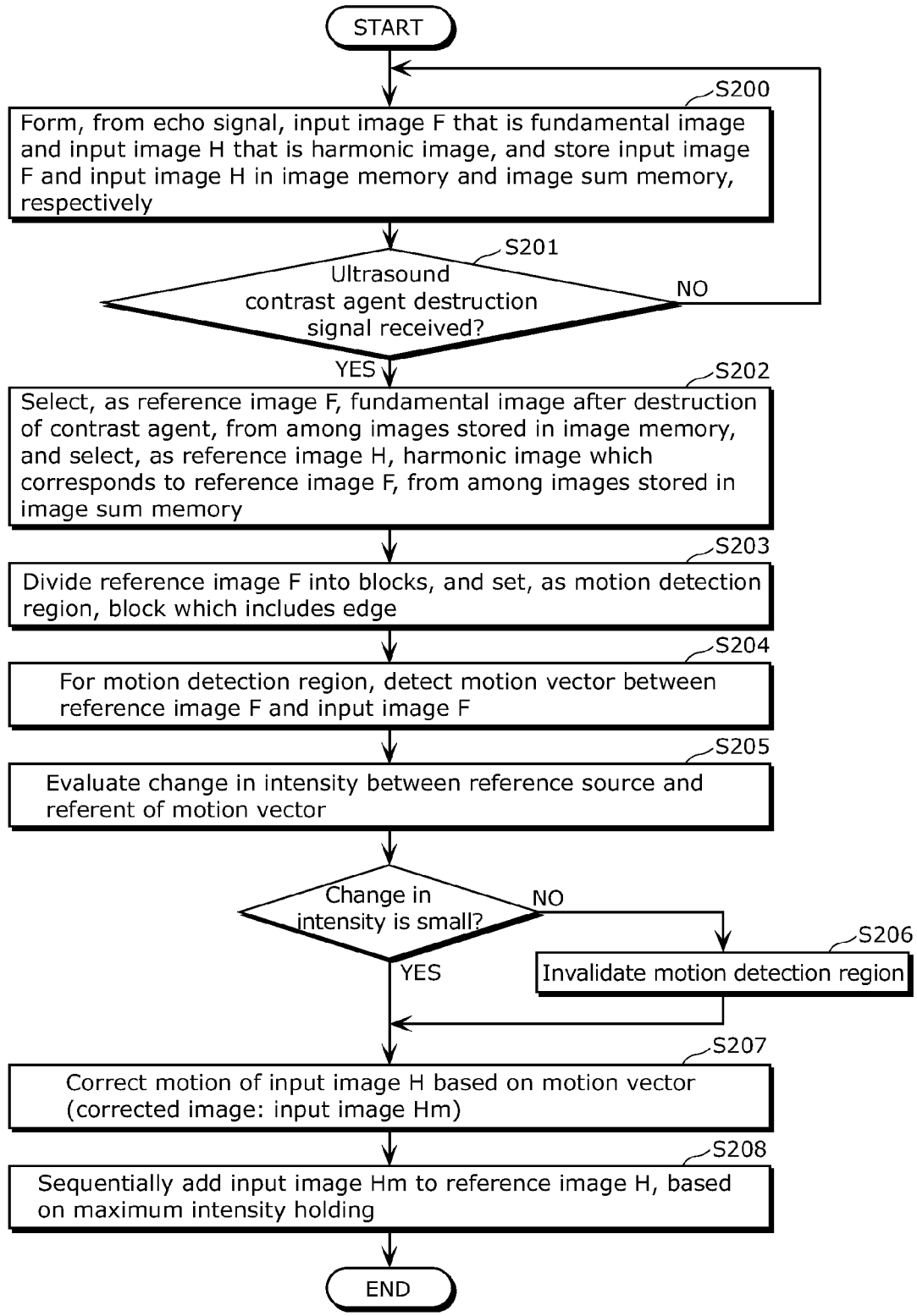
FIG. 4A is a flowchart according to Embodiment 2.

The following describes, using FIG. 4A, a flow of operations performed in Embodiment 2.

FIG. 4A is a flowchart according to Embodiment 2.

[Step S200]

First, as with Embodiment 1, from an echo signal, the fundamental imaging unit 204 forms the input image F which is formed from a fundamental component and stores the input image F in the image memory 206, and the harmonic imaging unit 205 forms the input image H which is formed from a harmonic component and stores the input image H in the image sum memory 207. In addition, the fundamental imaging unit 204 outputs the input image F to the motion detection unit 209 and the enhancement determination unit 210. Furthermore, the harmonic imaging unit 205 outputs the input image H to the motion correction unit 211.

[Step S201]

Next, the motion detection region setting unit 208 transits to a waiting state waiting for an operation of control on the ultrasound contrast agent destruction performed by a user. When a destruction signal is not input, the motion detection region setting unit 208 returns to Step S200, and generates an image from the next echo signal.

[Step S202]

When the ultrasound contrast agent destruction signal is received, the motion detection region setting unit 208 selects, as the reference image F, an image obtained immediately after the destruction of the ultrasound contrast agent, from among one or more of the fundamental images stored in the image memory 206. In a similar manner, as the reference image H, the harmonic image which is obtained immediately after the destruction of the ultrasound contrast agent is selected from among one or more of the harmonic images stored in the image sum memory 207.

[Step S203]

Next, the motion detection region setting unit 208 performs an edge determination on each of the blocks included in the reference image F. The motion detection region setting unit 208 performs edge determination according to (Expression 2) as with Embodiment 1, and sets, as the motion detection region, a block which includes the edge.

[Step S204]

Next, for the motion detection region set by the motion detection region setting unit 208, the motion detection unit 209 performs a pattern matching to detect the motion vector between the reference image F and the input image F.

[Step S205]

Next, the enhancement determination unit 210 determines whether a contrast enhancement is present or absent in the referent of the motion vector. Specifically, as with Embodiment 1, the enhancement determination unit 210 evaluates the change in intensity between the reference image F that is the reference source of the motion vector and the input image F that is the referent of the motion vector. The enhancement determination unit 210 evaluates the change in intensity by determining that the block which satisfies the (Expression 4) is not under the contrast enhancement, and sets such the block as the non-enhanced region, where C represents an average intensity of a block included in the reference image, D represents an average intensity value of a block included in the input image, T represents a threshold value, and n represents the number of the pixels included in a block.

[Math. 4]

$$|C - D| < T, C = \sum_{i=1}^{n} C_i/n, D = \sum_{i=1}^{n} D_i/n \quad \text{(Expression 4)}$$

Here, the threshold value T is set to, for example, a value that is 10% of the dynamic range of an image.

[Step S206]

It should be noted that, when a block is set as the enhanced region, the enhancement determination unit 210 invalidates the motion vector.

[Step S207]

In addition, as with Embodiment 1, the motion correction unit 111 performs a translation processing using the detected motion vector, and corrects misalignment of the input image F with respect to the reference image F.

[Step S208]

Lastly, as with Embodiment 1, the image sum unit 212 constructs a micro-vessel pattern from the harmonic image F with maximum intensity holding.

The operation performed in Embodiment 2 is as described above.

(Effect)

In Embodiment 2, it is determined whether the referent of the motion vector is enhanced with ultrasound contrast agent. If the referent is under the contrast enhancement, the motion vector thereof is not used. Thus, as with Embodiment 1, it is possible to realize the motion detection in which the influence of contrast enhancement is removed.

Variation 1 of Embodiment 2

Figure 10:
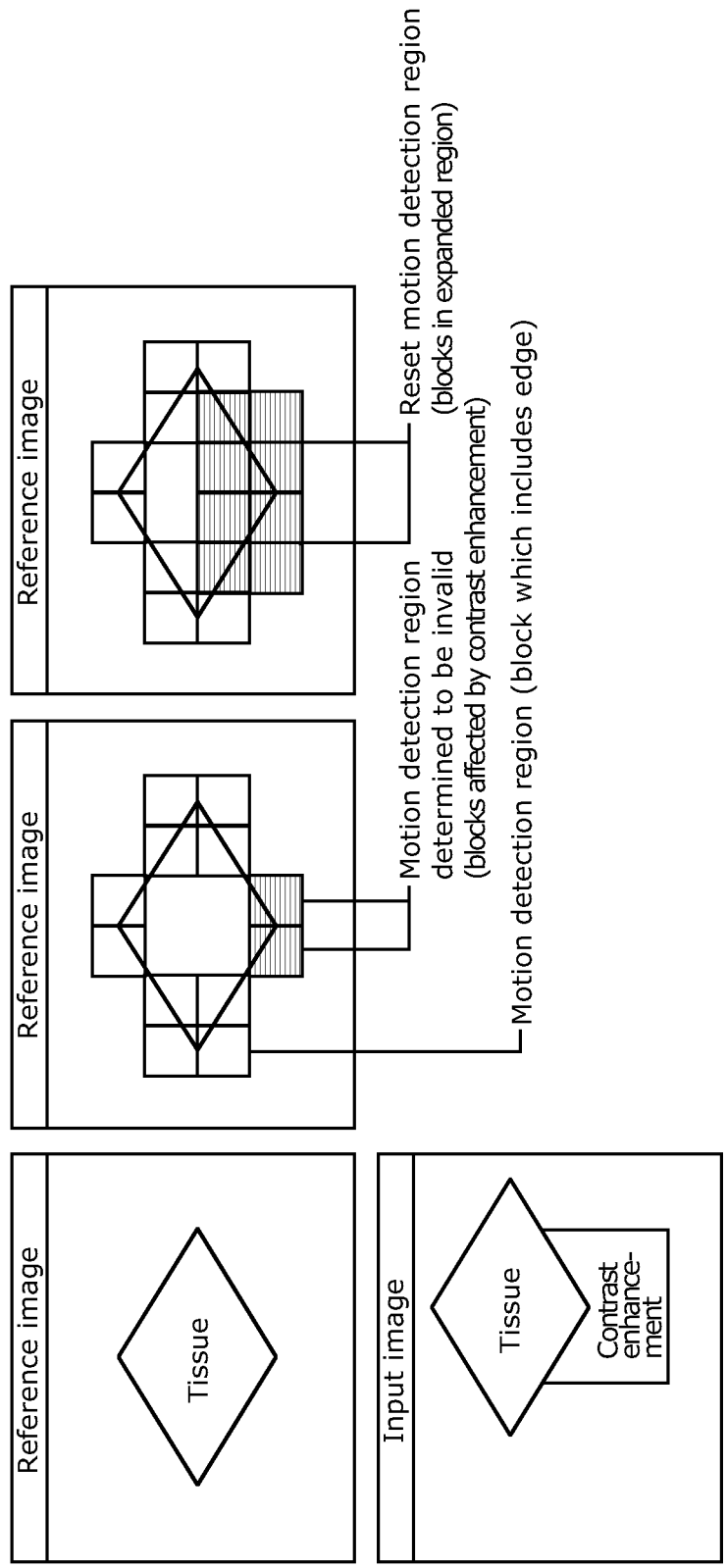
FIG. 10 is a diagram for describing a resetting of a motion detection region.
Figure 11:
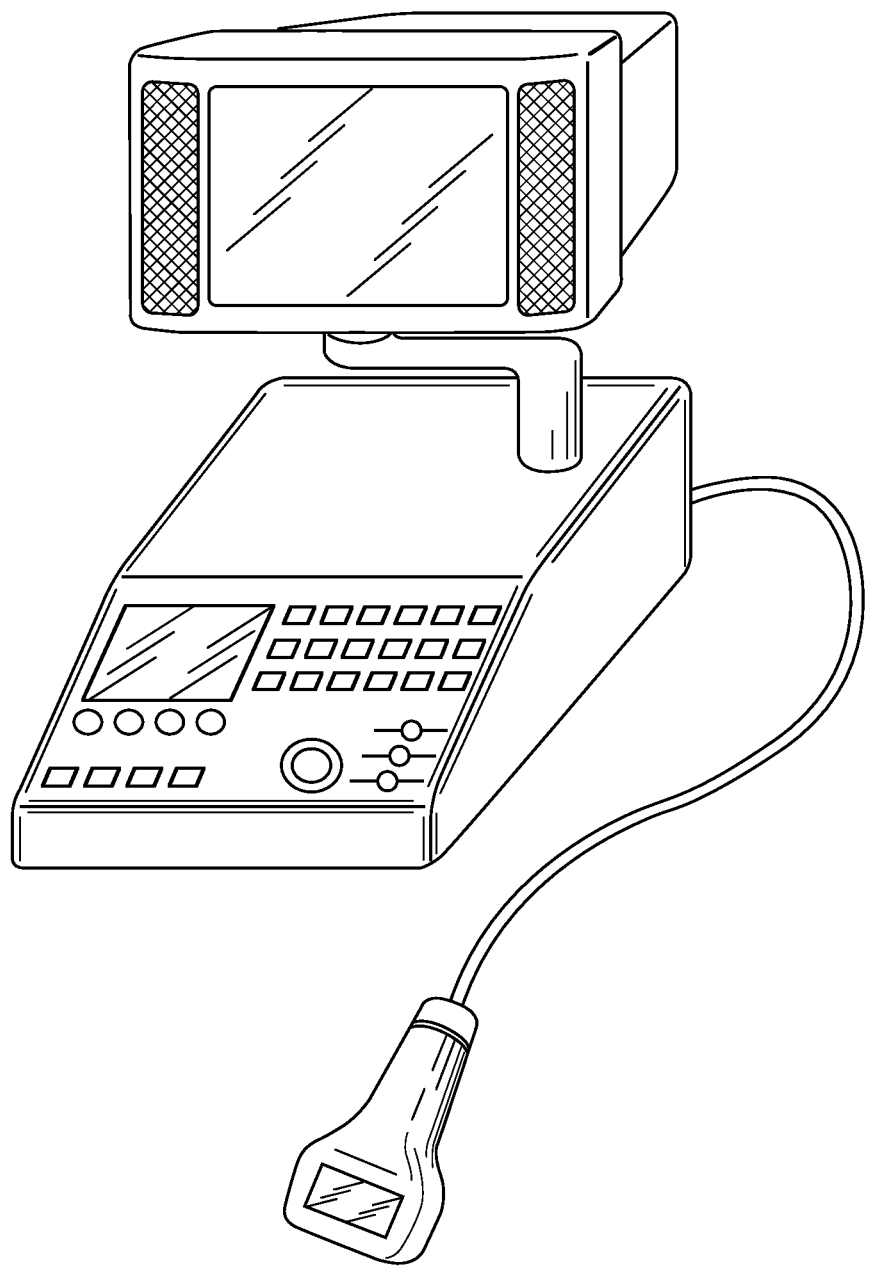
FIG. 11 is an example of an external view of an ultrasound diagnostic apparatus.

In the above, when the referent of the motion vector is under the contrast enhancement, the motion vector thereof is invalidated and the motion vector of the blocks around the referent is adopted. However, as shown in FIG. 10, the motion detection region may be expanded so as to include the block which includes the edge, and the motion vector may be detected again.

Furthermore, in the enhancement determination in Step S204, the determined is made based on the difference in the average intensity of respective blocks. However, the enhancement determination is not limited to such an example, but the determination may be made based on the pattern similarity, such as sum-of-absolute difference (SAD) or the like.

Furthermore, as with Embodiment 1, the motion correction may be performed by off-line processing.

Furthermore, although the above has been described with the example of the FRI, the above description can also be applied to a diagnostic method based on the TIC, as with Embodiment 1.

As described above, according to an exemplary embodiment disclosed herein, when an contrast enhancement appears in a region which is objectively believed to have a small enhancement and set as a region used for the position adjustment, it is possible to reset a region to be used for the position adjustment thereafter and continue the obtainment of the ultrasound diagnostic image.

Furthermore, when a contrast enhancement appears in the region which is objectively believed to have a small enhancement and set as the region for the position adjustment, it is possible to increase the size of the region for the position adjustment, and accurately detect the feature of the image for the position adjustment.

Variation 2 of Embodiment 2

The following describes Variation 2 of Embodiment 2 of the present disclosure. This variation describes an example in which the position adjustment is performed using, from the fundamental image and the harmonic image formed from the echo signal obtained from the subject, the harmonic image.

Figure 4B:
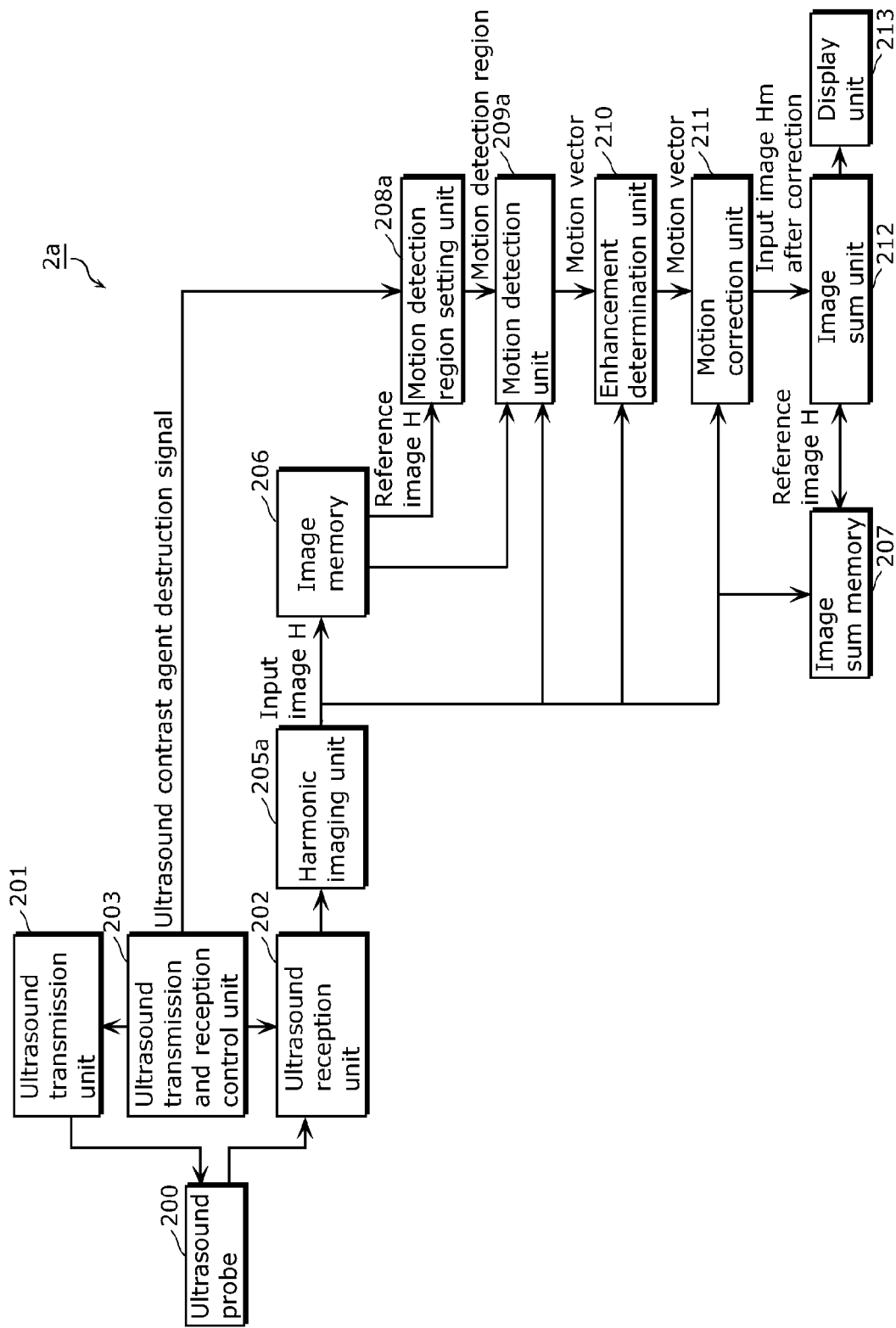
FIG. 4B is a configuration diagram of an ultrasound diagnostic apparatus according to Variation 2 of Embodiment 2.

FIG. 4B is a configuration diagram of an ultrasound diagnostic apparatus 2a according to this variation.

As shown in FIG. 4B, the ultrasound diagnostic apparatus 2a according to this variation includes: the ultrasound probe 200, the ultrasound transmission unit 201, the ultrasound reception unit 202, the ultrasound transmission and reception control unit 203, a harmonic imaging unit 205a, the image memory 206, the image sum memory 207, a motion detection region setting unit 208a, the motion detection unit 209a, the enhancement determination unit 210, the motion correction unit 211, the image sum unit 212, and the display unit 213. A significant difference between this variation and Embodiment 2 is that this variation does not include the fundamental imaging unit 204.

(Configuration)

The following describes only configuration blocks which are different from the configuration blocks in Embodiment 2.

The ultrasound reception unit 202 converts the echo signal output from the ultrasound probe 200 into a digital signal, and then outputs the digital signal to the harmonic imaging unit 205a.

The harmonic imaging unit 205a extracts a harmonic component from an echo signal output from the ultrasound reception unit 202, and converts the harmonic component into an intensity signal to form a harmonic image. Then, the harmonic imaging unit 205a outputs, as an input image H, the formed harmonic image to each of the image memory 206, the motion detection unit 209a, the image sum memory 207, and the motion correction unit 211.

The motion detection region setting unit 208a selects, as the image pair, a contrast enhanced image H including great amount of images of the ultrasound contrast agent and a reference image H including a small amount of images of the ultrasound contrast agent, from among the harmonic images stored in the image memory 206. Then, based on the selected image pair, the motion detection region setting unit 208a sets the motion detection region. The set motion detection region is output to the motion detection unit 209a.

The motion detection unit 209a detects, based on the motion detection region output from the motion detection region setting unit 208a, the motion vector between the images of the reference image H selected by the motion detection region setting unit 208a and the input image H output from the harmonic imaging unit 205a. The detected motion vector is output to the motion correction unit 211.

Other function blocks are the same as those in Embodiment 2, and thus the descriptions thereof are omitted.

(Operation)

Figure 4C:
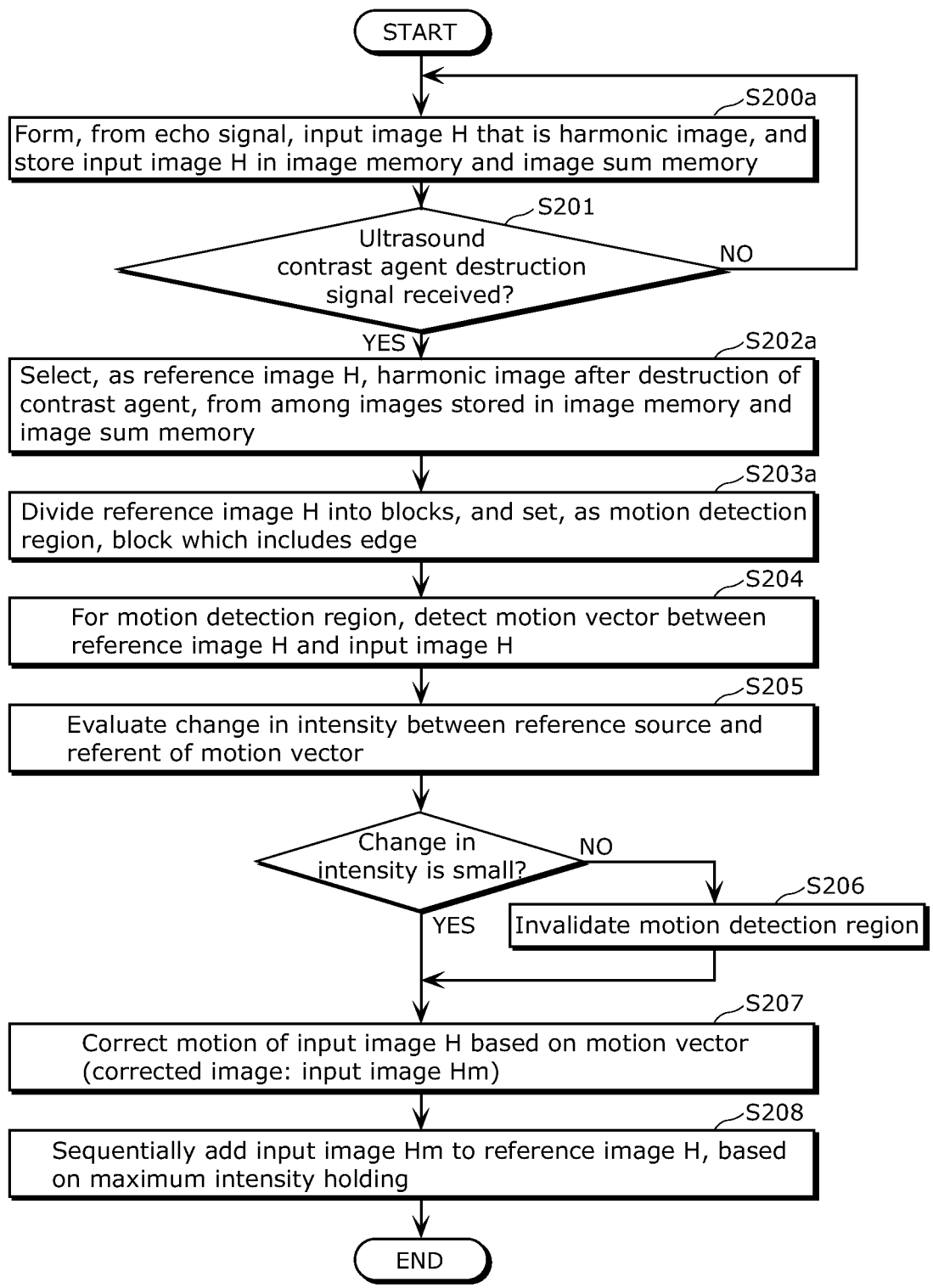
FIG. 4C is a flowchart according to Variation 2 of Embodiment 2.
Figure 6:
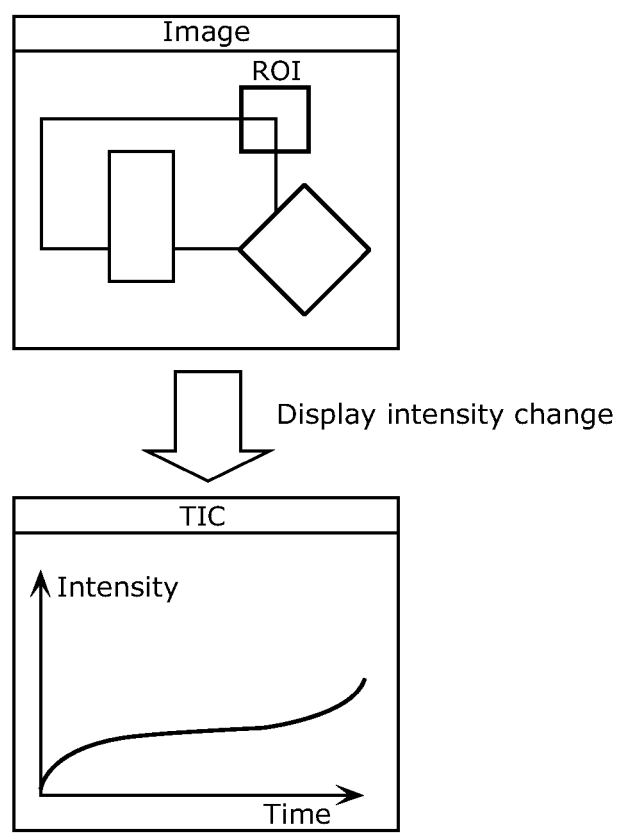
FIG. 6 is a diagram for describing an analysis on change over time.

FIG. 4C is a flowchart according to this variation.

The following describes only operations which are different from the operations performed in Embodiment 2. In this variation, instead of Step S200 in Embodiment 2, Step S200a is executed. Furthermore, instead of Step S202, Step S202a is executed.

[Step S200a]

First, the harmonic imaging unit 205 forms the input image H which is formed from the harmonic component included in the echo signal, and stores the input image H in each of the image memory 206 and the image sum memory 207. In addition, the harmonic imaging unit 205 outputs the input image H to each of the motion detection unit 209a, the enhancement determination unit 210, and the motion correction unit 211.

[Step S202a]

When the ultrasound contrast agent destruction signal is received, the motion detection region setting unit 208a selects, as the reference image H, an image immediately after the destruction of the ultrasound contrast agent, from among one or more of the harmonic images stored in each of the image memory 206 and the image sum memory 207.

[Step S203a]

Next, the motion detection region setting unit 208 performs an edge determination on each of the blocks included in the reference image H. The motion detection region setting unit 208 performs the edge determination according to (Expression 2) as with Embodiment 1, and sets the block which includes the edge as the motion detection region.

The other operations are the same as those performed in Embodiment 2, except that the processing performed on the reference image F in Embodiment 2 is performed on the reference image H, and the processing performed on the input image F in Embodiment 2 is performed on the input image H.

According to this variation, the misalignment that occurs between the images enhanced with the ultrasound contrast agent can be corrected using, from the fundamental image and the harmonic image, the harmonic image.

It should be noted that the function blocks included in the ultrasound diagnostic apparatus may be disposed at any position of the ultrasound diagnostic apparatus. For example, the function block of the ultrasound diagnostic apparatus may be disposed in the display screen or disposed in the ultrasound probe.

As described above, according to an exemplary embodiment disclosed herein, the ultrasound diagnostic apparatus can output, as the ultrasound diagnostic image, an image which is formed from the harmonic component that clearly captures the image of the ultrasound contrast agent. Furthermore, when a diagnosis is made off-line, the fundamental image is not necessary, and thus it is possible to reduce the capacity load of the record server.

Other Variations

The herein disclosed subject matter is to be considered descriptive and illustrative only, and the appended Claims are of a scope intended to cover and encompass not only the particular embodiments disclosed, but also equivalent structures, methods, and/or uses, and includes the below, for example.

(1) Each of the above apparatuses is specifically a computer system that includes a microprocessor, a ROM, a RAM, a hard disk unit, a display unit, a keyboard, a mouse, and the like. A computer program is stored in the RAM or the hard disk unit. Functions of each of the apparatuses can be accomplished through the operation of the microprocessor in accordance with the computer program. The computer program mentioned here is a combination of a plurality of instruction codes that represent instructions to a computer for achieving predetermined functions.

(2) The components that constitute each of the above apparatuses may be partly or wholly realized by one system LSI (Large Scale Integration). The system LSI is an ultra-multifunctional LSI produced by integrating a plurality of components on one chip, and is specifically a computer system that includes a microprocessor, a ROM, a RAM, and the like. A computer program is stored in the RAM. Functions of the system LSI can be accomplished through the operation of the microprocessor in accordance with the computer program.

(3) The components that constitute each of the above apparatuses may be partly or wholly realized by an IC card or a single module that is removably connectable to the apparatus. The IC card or the module is a computer system that includes a microprocessor, a ROM, a RAM, and the like. The IC card or the module may include the above-mentioned ultra-multifunctional LSI. Functions of the IC card or the module can be accomplished through the operation of the microprocessor in accordance with the computer program. The IC card or the module may be tamper resistant.

(4) The present disclosure may also be the method described above. The present disclosure may also be a computer program that realizes the method by a computer. The present disclosure may also be a digital signal formed by the computer program.

The present disclosure may also be a computer-readable recording medium, such as a flexible disk, a hard disk, a CD-ROM, an MO, a DVD, a DVD-ROM, a DVD-RAM, a BD (Blu-ray Disc), or a semiconductor memory, on which the computer program or the digital signal is recorded. Furthermore, the present disclosure may be the digital signal recorded on such a recording medium.

The present disclosure may also be the computer program or the digital signal transmitted via an electric communication line, a wired or wireless communication line, a network such as the Internet, data broadcasting, and the like.

The present disclosure may also be a computer system that includes a microprocessor and a memory. In this case, the computer program may be stored in the memory, with the microprocessor operating in accordance with the computer program.

The computer program or the digital signal may be provided to another independent computer system by distributing the recording medium on which the computer program or the digital signal is recorded, or by transmitting the computer program or the digital signal via the network and the like. The independent computer system may then execute the computer program or the digital signal to function as the present disclosure.

(5) The above embodiments and variations may be freely combined.

Each of the structural elements in each of the above-described embodiments may be configured in the form of an exclusive hardware product, or may be realized by executing a software program suitable for the structural element. Each of the structural elements may be realized by means of a program executing unit, such as a CPU and a processor, reading and executing the software program recorded on a recording medium such as a hard disk or a semiconductor memory. Here, the software program for realizing the ultrasound diagnostic apparatus according to each of the embodiments is a program described below.

The program causes a computer to execute: forming images each of which corresponds to one of echo signals received from the subject; selecting a first image from among images which include images of the ultrasound contrast agent, selecting a second image from among images which do not include images of the ultrasound contrast agent, and setting, as a motion detection region, a region in which an amount of image change between the first image and the second image is smaller than a predetermined amount, the images which include images of the ultrasound contrast agent and the images which do not include images of the ultrasound contrast agent being included in the images formed in the forming; and outputting, as an ultrasound diagnostic image, the second image on which a position adjustment has been performed to match a position of the motion detection region set in the setting and a position of a region included in the second image and similar in an image feature to the motion detection region.

The herein disclosed subject matter is to be considered descriptive and illustrative only, and the appended Claims are of a scope intended to cover and encompass not only the particular embodiments disclosed, but also equivalent structures, methods, and/or uses.

INDUSTRIAL APPLICABILITY

The method of detecting a motion under administration of the ultrasound contrast agent according to one or more exemplary embodiments disclosed herein are useful to correct unsteady movement of hand or body motion under the contrast enhancement, and applicable to, for example, microvessel imaging based on the maximum intensity holding described in the above exemplary embodiments, and a tumor type differentiation based on the diagnostic method based on the TIC.

The invention claimed is:

1. An ultrasound diagnostic apparatus which outputs an ultrasound diagnostic image of a subject to which an ultrasound contrast agent has been administered, the ultrasound diagnostic apparatus comprising:
an ultrasound probe which transmits ultrasound to the subject and which receives echo signals reflected back from the subject;
imaging means for forming images from fundamental components of the echo signals received by the ultrasound probe from the subject and for forming images from harmonic components of the echo signals received by the ultrasound probe from the subject, any one of the images corresponding to any one of the echo signals received from the subject;
motion detection region setting means for selecting a first image from among the images formed from the fundamental components of the echo signals, selecting a second image that is different from the first image from among the images formed from the fundamental components of the echo signals, and setting, as a motion detection region, a region of a portion of the first image and a portion of the second image;
detection means for detecting an amount of movement between the first image and the second image in the motion detection region; and
correction means for performing, based on the amount of movement detected, a position adjustment of a third image formed from the harmonic components of the same echo signal from which the first image was formed, such that a position of the third image is corrected to match a position of the second image.

2. The ultrasound diagnostic apparatus according to claim 1, wherein the motion detection region setting means sets, as the motion detection region, a region which is among a plurality of regions included in the first image and has (i) an intensity gradient greater than a predetermined value and (ii) an amount of intensity change smaller than a predetermined value between the first image and the second image.

3. The ultrasound diagnostic apparatus according to claim 1, further comprising output means for, when the third image includes a plurality of third images, outputting, as an ultrasound diagnostic image, an image obtained by summing the third images on which the position adjustment has been performed.

4. The ultrasound diagnostic apparatus according to claim 1, wherein the motion detection region setting means selects, as the first image, an image formed at a point in time before the ultrasound contrast agent is destroyed through generation of ultrasound having a high sound pressure by the ultrasound probe, and selects, as the second image, an image formed at a point in time after the ultrasound contrast agent has been destroyed, to set the motion detection region.

5. The ultrasound diagnostic apparatus according to claim 1, wherein the motion detection region setting means selects the first image and the second image to obtain a biggest difference between an average intensity of the first image and an average intensity of the second image, to set the motion detection region.

6. The ultrasound diagnostic apparatus according to claim 1, further comprising:
a sensor which measures a position or an angle of the ultrasound probe relative to the subject, when the ultrasound probe receives each of the echo signals,
wherein the motion detection region setting means selects the first image and the second image to obtain a difference smaller than or equal to a predetermined value between a value measured by the sensor when the first image is formed and a value measured by the sensor when the second image is formed, to set the motion detection region.

7. The ultrasound diagnostic apparatus according to claim 1, wherein the motion detection region setting means selects, as one of the first image and the second image, an image which is among the images and has an average intensity greater than or equal to a predetermined value, and selects, as the other of the first image and the second image, an image which is among the images and has an average intensity smaller than or equal to the predetermined value, to set the motion detection region.

8. The ultrasound diagnostic apparatus according to claim 1, further comprising enhancement determination means for determining whether or not a difference between an average intensity of the motion detection region in the first image and an average intensity of a region which is in the second image and corresponds to the motion detection region is greater than a predetermined value,
wherein when the enhancement determination means determines that the difference in the average intensity is greater than the predetermined value, the motion detection region setting means resets the motion detection region.

9. The ultrasound diagnostic apparatus according to claim 8, wherein, when the enhancement determination means determines that the difference in the average intensity is greater than the predetermined value, the motion detection region setting means resets the motion detection region by setting, as a new motion detection region, a region which includes the motion detection region.

10. The ultrasound diagnostic apparatus according to claim 1, wherein the motion detection region setting means determines, from among regions which are included in the first image and each include sub-regions, a region having a largest intensity gradient, and sets, as the motion detection region, the region having the largest intensity gradient which is a region in which a difference in average intensity of each of the sub-regions is largest.

11. A method for an ultrasound diagnostic apparatus which outputs an ultrasound diagnostic image of a subject to which an ultrasound contrast agent has been administered, the ultrasound diagnostic apparatus comprising an ultrasound probe, the method comprising:
transmitting, with the ultrasound probe, ultrasound to the subject and receiving, with the ultrasound probe, echo signals reflected back from the subject;
forming images from fundamental components of the echo signals received by the ultrasound probe from the subject and forming images from harmonic components of the echo signals received by the ultrasound probe from the subject, any one of the images corresponding to any one of the echo signals received from the subject;
selecting a first image from among the images formed from the fundamental components of the echo signals, selecting a second image that is different from the first image from among the images formed from the fundamental components of the echo signals, and setting, as a motion detection region, a region of a portion of the first image and a portion of the second image;
detecting an amount of movement between the first image and the second image in the motion detection region; and
performing, based on the amount of movement detected, a position adjustment of a third image formed from the harmonic components of the same echo signal from which the first image was formed, such that a position of the third image is corrected to match a position of the second image.

12. A non-transitory computer-readable recording medium which stores a computer program that is executable by a computer of an ultrasound diagnostic device that comprises an ultrasound probe, the program being executable by the computer to cause the computer to execute functions comprising:
- transmitting, with the ultrasound probe, ultrasound to the subject and receiving, with the ultrasound probe, echo signals reflected back from the subject;
- forming images from fundamental components of the echo signals received by the ultrasound probe from the subject and forming images from harmonic components of the echo signals received by the ultrasound probe from the subject, any one of the images corresponding to any one of the echo signals received from the subject;
- selecting a first image from among the images formed from the fundamental components of the echo signals, selecting a second image that is different from the first image from among the images formed from the fundamental components of the echo signals, and setting, as a motion detection region, a region of a portion of the first image and a portion of the second image;
- detecting an amount of movement between the first image and the second image in the motion detection region; and
- performing, based on the amount of movement detected, a position adjustment of a third image formed from the harmonic components of the same echo signal from which the first image was formed, such that a position of the third image is corrected to match a position of the second image.

13. The ultrasound diagnostic apparatus according to claim 1, wherein the first image includes the ultrasound contrast agent and the second image includes less of the ultrasound contrast agent than the ultrasound contrast agent than the first image.

14. The ultrasound diagnostic apparatus according to claim 1, wherein the motion detection region setting means sets, as the motion detection region, a region in which an amount of image change between the first image and the second image is smaller than a predetermined amount.

15. The ultrasound diagnostic apparatus according to claim 1, wherein the correction means performs the position adjustment according to partial translation of the amount of movement.

16. The method according to claim 11, further comprising:

destroying the ultrasound contrast agent through generation of ultrasound directed to the subject by the ultrasound probe,
wherein an image formed before the destroying of the ultrasound contrast agent is selected as the first image and an image formed after the destroying of the ultrasound contrast agent is selected as the second image.

17. The method according to claim 11, wherein the first image includes the ultrasound contrast agent and the second image includes less of the ultrasound contrast agent than the first image.

18. The method according to claim 11, wherein the motion detection region is a region in which an amount of image change between the first image and the second image is smaller than a predetermined amount.

19. The method according to claim 11, wherein the motion detection region is a region which is among a plurality of regions included in the first image and has (i) an intensity gradient greater than a predetermined value and (ii) an amount of intensity change smaller than a predetermined value between the first image and the second image.

20. The method according to claim 11, wherein selecting the first image and the second image is performed to obtain a biggest difference between an average intensity of the first image and an average intensity of the second image, to set the motion detection region.

21. The method according to claim 11, further comprising:
measuring a position or an angle of the ultrasound probe relative to the subject, when the ultrasound probe receives each of the echo signals,
wherein selecting the first image and the second image is performed to obtain a difference smaller than or equal to a predetermined value between a value measured by the sensor when the first image is formed and a value measured by the sensor when the second image is formed, to set the motion detection region.

22. The method according to claim 11, further comprising:
destroying the ultrasound contrast agent through generation of ultrasound directed to the subject by the ultrasound probe,
wherein an image formed after the destroying of the ultrasound contrast agent is selected as the second image and an image formed after the forming of the second image after a predetermined period of time has elapsed from the destroying of the ultrasound contrast agent is selected as the first image.

* * * * *